US011478409B2

(12) United States Patent
Paes et al.

(10) Patent No.: US 11,478,409 B2
(45) Date of Patent: Oct. 25, 2022

(54) ANTI-WRINKLE COSMETIC COMPOSITION, COMPOSITION SYSTEM AND METHOD FOR COSMETIC SKIN TREATMENT

(71) Applicant: Natura Cosméticos S.A., São Paulo (BR)

(72) Inventors: Fabiana Paes, São Paulo (BR); Clarissa Capelas Romeu, São Paulo (BR); Eduardo Alexandre De Oliveira Reis, São Paulo (BR); Joice Panzarin Savietto, São Paulo (BR); Kassandra Tadini D'Annolfo, São Paulo (BR); Priscila Carollo Moncayo, São Paulo (BR); Ricardo Augusto Santos De Oliveira, São Paulo (BR); Simone Andrea Emidio, São Paulo (BR); Soraya Baione De Moura, Jundiaí (BR); Daniela Zimbardi, São Paulo (BR)

(73) Assignee: Natura Cosmeticos S.A., Sao Paula (BR)

( * ) Notice: Subject to any disclaimer, the term of this patent is extended or adjusted under 35 U.S.C. 154(b) by 0 days.

(21) Appl. No.: 16/304,530

(22) PCT Filed: May 24, 2017

(86) PCT No.: PCT/BR2017/050127
§ 371 (c)(1),
(2) Date: Nov. 26, 2018

(87) PCT Pub. No.: WO2017/201596
PCT Pub. Date: Nov. 30, 2017

(65) Prior Publication Data
US 2019/0167540 A1 Jun. 6, 2019

(30) Foreign Application Priority Data

| May 24, 2016 | (BR) | 102016011784-4 |
| May 24, 2016 | (BR) | 102016011785-2 |
| May 24, 2016 | (BR) | 102016011793-3 |
| Sep. 15, 2016 | (BR) | 102016021328-2 |

(51) Int. Cl.
A61Q 19/08 (2006.01)
A61Q 19/00 (2006.01)
A61K 9/107 (2006.01)
A61K 8/06 (2006.01)
A61K 8/04 (2006.01)
A61K 8/9789 (2017.01)
A61K 8/92 (2006.01)
A61K 8/9728 (2017.01)
A61Q 17/04 (2006.01)

(52) U.S. Cl.
CPC .............. *A61K 8/062* (2013.01); *A61K 8/922* (2013.01); *A61K 8/9728* (2017.08); *A61K 8/9789* (2017.08); *A61Q 17/04* (2013.01); *A61Q 19/08* (2013.01)

(58) Field of Classification Search
CPC ................ A61K 45/06; A61K 2300/00; A61K 2800/10; A61K 38/011; A61K 9/0014; A61K 2800/522; A61K 9/06; A61K 9/0012; A61K 8/062; A61K 8/06; A61K 8/068; A61Q 19/08; A61Q 19/00; A61Q 17/04
See application file for complete search history.

(56) References Cited

U.S. PATENT DOCUMENTS

| 2004/0028643 A1* | 2/2004 | Chiba | A61K 8/9789 424/74 |
| 2005/0124705 A1* | 6/2005 | Schreiber | A61K 8/0208 516/53 |
| 2005/0276833 A1* | 12/2005 | Fowler | A61K 8/06 424/405 |
| 2011/0305735 A1* | 12/2011 | Cebrian Puche | A61K 8/64 424/401 |
| 2012/0041064 A1* | 2/2012 | Ogbourne | A61K 8/375 514/549 |
| 2012/0058061 A1* | 3/2012 | Nguyen | A61K 8/14 424/59 |
| 2012/0164121 A1* | 6/2012 | Paufique | A61K 8/99 424/93.51 |
| 2013/0078294 A1 | 3/2013 | Alexiades-Armenakas | |
| 2013/0251644 A1 | 9/2013 | Majhi et al. | |

(Continued)

FOREIGN PATENT DOCUMENTS

| JP | 2003055190 A | 2/2003 |
| WO | WO 2007/033453 A1 | 3/2007 |

(Continued)

OTHER PUBLICATIONS

Prospector. Uplevity peptide solution. Date retrieved: Mar. 23, 2021. <https://www.ulprospector.com/en/na/PersonalCare/Detail/2670/236359/Uplevity-peptide-solution>. (Year: 2021).*

(Continued)

*Primary Examiner* — Tracy Liu
(74) *Attorney, Agent, or Firm* — Alston & Bird LLP

(57) ABSTRACT

The present invention relates to gel cream anti-aging cosmetic compositions in the form of an oil-in-water emulsion comprising sensory ingredients that are suitable for the complete treatment of the skin and also provide specific benefits for day and night care, which complement each other.

6 Claims, 11 Drawing Sheets

(56) References Cited

U.S. PATENT DOCUMENTS

| | | | |
|---|---|---|---|
| 2014/0234236 A1* | 8/2014 | Prendergast | A61K 8/37 424/59 |
| 2015/0202139 A1* | 7/2015 | Friedman | A61K 8/35 424/450 |
| 2016/0067166 A1 | 3/2016 | Brock et al. | |
| 2016/0175217 A1* | 6/2016 | Kim | A61K 8/498 514/456 |
| 2017/0333491 A1* | 11/2017 | Soley Astals | A61P 17/18 |

FOREIGN PATENT DOCUMENTS

| | | |
|---|---|---|
| WO | WO 2008/079898 A1 | 7/2008 |
| WO | WO 2015031971 A2 | 3/2015 |

OTHER PUBLICATIONS

International Search Report and Written Opinion for International Applicaton No. PCT/BR2017/050127 dated Aug. 16, 2017.

International Preliminary Report on Patentability for International Application No. PCT/BR2017/050127 dated Sep. 24, 2018, 11 pages.

Extended European Search Report for European Application No. 17801852.9 dated Dec. 2, 2019, 11 pages.

"Satin Firming Night Creme", GNPD, MINTEL, (Nov. 25, 2015), [retrieved May 15, 2020]. Retrieved from the Internet: <URL: https://www.gnpd.com/sinatra/recordpage/3582201/from_search/6e3fSe0WTo/?page=1>, 3 pages.

"Lifting Lotion", GNPD, MINTEL, (Mar. 9, 2016), [retrieved May 15, 2020]. Retrieved from the Internet: <URL: https://www.gnpd.com/sinatra/recordpage/3772751/from_search/0Nff4wSFqZ/?page=1>, 3 pages.

"Radiant CC Crème SPF 20/PA+", GNPD, MINTEL, (Aug. 21, 2014), [retrieved May 15, 2020]. Retrieved from the Internet: <URL: https://www.gnpd.com/sinatra/recordpage/2534029/from_search/z5y2VRi6oW/?page=1>, 3 pages.

"High Performance Anti-Aging Cream", GNPD, MINTEL, (Oct. 6, 2011), [retrieved May 15, 2020]. Retrieved from the Internet: <URL: https://www.gnpd.com/sinatra/recordpage/1649146/from_search/FsnqEinlG1/?page=1>, 7 pages.

* cited by examiner

ANTI-WRINKLE COSMETIC COMPOSITION, COMPOSITION SYSTEM AND METHOD FOR COSMETIC SKIN TREATMENT

FIELD OF THE INVENTION

The present invention relates to gel cream anti-aging cosmetic compositions in the form of an oil-in-water emulsion comprising sensory ingredients that are suitable for the complete treatment of the skin and also provide specific benefits for day and night care, which complement each other.

PRIOR ART

Skin aging is the result of several factors. In addition to the individual genetic predisposition, there are external factors and style- and quality of life-related factors that cause our organism, including the skin, to undergo changes and decelerations of various physiological processes.

It is known that after the age of thirty (30) six major physiological mechanisms of the skin are impaired, it being possible to notice some signs of skin aging caused by the deceleration of some physiological processes.

The affected mechanisms are:
1. cell renewal;
2. skin defense systems against free radicals, which can cause loss of cellular energy;
3. repeated facial movements cause the formation of creases from micro tensions on the skin;
4. loss of the natural moisturizing barrier of the skin;
5. reduction in the elastic system precursors of the skin; and
6. reduction in skin collagen precursors.

After the age of forty-five (45), seven (7) physiological mechanisms of the skin are impaired:
1. increased reduction of collagen production and density;
2. reduction in precursors and disarrangement of collagen fibers;
3. glycation (stiffening) of collagen fibers;
4. increase of micro-lesions that cause wrinkles;
5. increased elastin breakdown;
6. loss of the natural moisturizing barrier of the skin; and
7. reduction in the elastic system precursors of the skin; and After the age of sixty (60), there are also seven (7) physiological mechanisms of the skin that are impaired:
1. Increased reduction in hyaluronic acid production, in addition to loss of density and disarrangement of the extracellular matrix fibers;
2. Increased reduction and disarrangement of the major elastic structures;
3. loss of functionality of the deeper layers of the skin;
4. increased breakdown of the extracellular matrix fibers;
5. loss of the natural moisturizing barrier of the skin;
6. reduction in the elastic system precursors of the skin; and
7. reduction in skin collagen precursors.

Ultimately, at the age of seventy (70), the seven (7) impaired physiological mechanisms of the skin are:
1. Increased reduction of the thickness of the skin causing it to be more fragile;
2. loss of skin barrier functionality;
3. reduction in the skin nutrients;
4. reduction in the skin's defense mechanisms.
5. reduction in the elastic system precursors of the skin;
6. reduction in skin collagen precursors; and
7. loss of the natural moisturizing barrier of the skin.

From among these external factors, environmental conditions considerably influence the body's functioning in general, since the human body has a rhythmic behavior, running cycles associated with the time (e.g., day and night).

In chronobiology (a science that studies biological phenomena from the chronological point of view) there are several rhythms associated with their length of time, including the circadian rhythm, which cycles are completed every 24 hours.

The skin does not "perceive" variations in light, however, it is subject to environmental agents such as temperature, moisture, mechanical and biological agents.

Some skin mechanisms present more robust scientific information on daily variations, for example:
Transepidermal water loss, subcutaneous blood flow intensity and amino acid content in the skin: these phenomena are much more marked at night;
Sebaceous glands secretion: the production of tallow and fat is greater during the day with its maximum peak at noon;
Skin temperature: the skin temperature varies according to the measured site; the skin temperature on the forearm achieves its maximum in the late afternoon, while on the face it reaches its maximum in the morning; at night, the skin temperature is lower.
Cell proliferation capacity that is higher around 11 PM and minimum around 12 PM.
Cellular healing mechanisms: most of the mapped genes related to such mechanism reach their peak activity during the day;
Leukocyte differentiation and cytokine production for immune response: most of the mapped genes related to such mechanism reach their peak activity during the day.

Therefore, the effect of a treatment may vary and may be dependent on the time of administration. Factors such as absorption, metabolization capacity, storage and affinity of a compound to cellular receptors may vary according to circadian rhythms.

To renew and recover the skin energy, it is not sufficient to treat just a single cause of the problem, but to act on all of them. To that end, an anti-aging treatment must act on the maintenance, stimulation and more effective regulation of the production of substances that constitute the skin, more intense cell renewal, recovery of natural moisturization combined with a stronger prevention against the main aggression mechanisms.

Existing products take care of only a few specific points, but not all the above mechanisms at the same time.

There is therefore a need for a composition acting on all these mechanisms simultaneously, providing an effective skin care treatment.

SUMMARY OF THE INVENTION

The present invention relates to anti-aging cosmetic compositions in the form of an oil-in-water emulsion, comprising:
a) at least one emollient;
b) at least one antioxidant;
c) at least one humectant;
d) at least one active ingredient;
e) at least one emulsifier;
f) at least one sensory modifier; and
g) cosmetically acceptable carriers.

Another object of the present invention relates to a composition system comprising a day care composition for and a night care composition.

A further object relates to a cosmetic treatment method of the skin which comprises applying the composition of the present invention.

DESCRIPTION OF THE INVENTION

Figure 1:
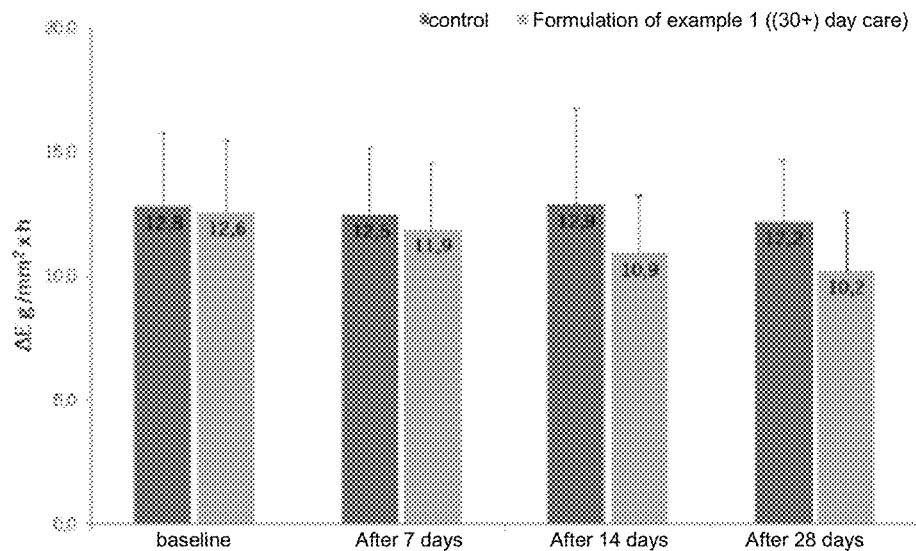
FIG. 1 shows a graph of the average variation in transepidermal water loss from the skin obtained in the beginning of the study and after 7, 14 and 28 days of use of (30+) compositions according to example 1 (day care) over the control.

The present invention relates to gel cream anti-aging cosmetic compositions in the form of an oil-in-water emulsion capable of treating simultaneously the six major physiological mechanisms of the skin, providing long-term benefits with progressive results over the period of treatment.

The six major physiological mechanisms according to the present invention include:
1. cell renewal;
2. protection of cellular energy;
3. relaxing of skin micro tensions;
4. recovery of the natural moisturizing barrier;
5. elastin stimulation; and
6. collagen stimulation.

Hereinafter, such mechanisms will be referred to as "the six major physiological mechanisms of the skin".

By "skin" is meant skin from the neck, face, arm, forearm, chest and hand.

By "anti-aging cosmetic compositions" is meant cosmetic compositions suitable for use in various age groups. Preferably, the age groups comprise ages over 30 years, particularly over 45 years, over 60 years and over 70 years.

For ease of reference, specific compositions for distinct age groups will be cited as: (30+) compositions referring to ages over 30 years; (45+) compositions referring to ages over 45 years; (60+) compositions referring to ages over 60 years; and (75+) compositions referring to ages over 60 years.

Another object of the present invention consists of a system of anti-aging, day care and night care cosmetic compositions, which complement each other, having suitable active ingredients for each period of the day.

Suitable active ingredients for each period in the present invention refer to are sunscreens, active ingredients having antioxidant activity and prolonged day-time hydration, and active ingredients for stimulating skin regeneration by eliminating toxins and deep night-time nutrition.

Yet another object of the invention is to provide cosmetic anti-aging compositions having a cream gel texture, which is easy to be applied on the skin, forming an emollient and wetting film without leaving a shiny and oily appearance.

The cream gel texture and its qualities according to the present invention are obtained by using low and medium molecular weight esters having high levels of volatile emollients that evaporate rapidly during application providing greater spreadability and fast absorption.

Therefore, the present invention relates to cosmetic cream gel anti-aging compositions in the form of an oil-in-water emulsion comprising at least one emollient, at least one antioxidant, at least one humectant, at least one active ingredient, at least one emulsifier, at least one sensory modifier and cosmetically acceptable carriers.

Another object of the present invention is a method for the cosmetic treatment of the skin comprising the topical application of a composition of the present invention on the skin to be treated, wherein the application takes place during the day and/or at night.

The anti-aging cosmetic compositions of the present invention comprise, in particular:
a) at least one emollient;
b) at least one antioxidant;
c) at least one humectant;
d) at least one active ingredient;
e) at least one emulsifier;
f) at least one sensory modifier; and
g) cosmetically acceptable carriers.

Emollients, without limiting the scope of the present invention, may be selected from caprylyl methicone, O12-15 alkyl benzoate, dibutyl adipate, dicaprylyl carbonate, isononyl isononanoate, dicapryl ether, dodecane, ethylhexyl palmitate, ethyl macadamate, isohexadecane, capric/caprylic triglyceride, butters from the Brazilian biodiversity, isoamyl cocoate or mixtures thereof.

Without being intended to limit the scope of the present invention, the following butters from the Brazilian bioversity may be used: murumuru butter which aids to replace skin barrier lipids providing repair and protection and resulting in decreased loss of water and maintenance of the natural skin hydration; Further butters such as those obtained from cocoa beans (*Theobroma cacao*), Cupuaçu (*Theobroma grandiflorum*), Ucuúba and Sapucainha, or mixtures thereof.

Butters aid in the lipid replacement of the skin barrier, providing repair and protection, which helps to reduce the loss of water and to maintain the natural skin hydration for longer periods of time.

Antioxidants, without being intended to limit the scope of the present invention, may be selected from butylated hydroxytoluene (BHT), tocopherol acetate or natural plant extracts, for example *Camellia sinensis* (green tea), *Theobroma cacao* (cocoa), *Spilanthes acmella* (Jambu) or mixtures thereof.

The polyphenols present in the green tea extract, mainly have the ability to interact with cell membranes and protect cells from oxidative processes, thus ensuring the proper functioning and protection of cell energy, also promoting cell renewal.

Humectants, without limiting the scope of the present invention, may be selected from sugar alcohols, such as glycols, glycerol, sorbitol, mannitol or mixtures thereof.

Preferably, the humectant is vegetable glycerin extracted from palm oil, which aids in surface hydration. Such effect coupled with the protection provided by butters promotes recovery of the natural moisturizing barrier of the skin.

The active ingredient of the present invention may be selected from peptides which are in general synthetic molecules, particularly acetyl-tetrapeptide-2, which acts on the stimulation of collagen and elastin production, thus promoting improved skin tone and elasticity.

The active ingredient may also be selected from *Hymenaea courbaril* extract; a mixture of sodium cocoyl amino acids/sarcosine/potassium aspartate/magnesium aspartate/propylene glycol; a mixture of *Paeonia albiflora* extract/phenoxyethanol/ethylhexylglycerin, *Cichorium intybus* extract; *Schinus Terebinthifolius* leaf extract; omega 6 passion fruit ceramide; or mixtures thereof.

When *Paeonia albiflora* and *Cichorium intybus* extracts are used, root extracts from these plants are particularly used.

Emulsifiers, without limiting the scope of the present invention, may be selected from at least one of glyceryl stearate citrate, potassium cetylphosphate, PEG-100, acrylates, xanthan gum, cetearyl alcohol, a mixture of glyceryl stearate/PEG-100, among others known in the art. state of the art, or mixtures thereof.

Sensory modifiers, without limiting the scope of the present invention, may be selected from silicones, such as cyclopentasiloxane, dimethicone or cyclopentasiloxane/dimethicone crospolymers, or other compounds such as titanium isopropyl triisostearate, nylon-12, polymethylsilsesquioxane, aluminum starch octenylsuccinate or mixtures thereof.

The compositions according to the present invention may further comprise a viscosity donor selected from acrylate/$C_{10-30}$ alkyl acrylate, carbopol, such as Carbopol ETD 2020, a mixture of hydroxuethylacrilate/sodium acryloyldimethyltaurate copolymer, squalene and polysorbate 60 (Simulgel NS), or mixtures thereof.

Cosmetically acceptable carriers may be selected from compounds known in the art. Examples of carriers are: preservatives, perfumes/fragrances, polymer neutralizers, chelating agents, pH adjusters, among others. Disodium EDTA (chelating agent), iodopropynyl butylcarbamate (preservative), phenoxyethanol (preservative), pataqueira essential oil (perfume) and triethanolamine (pH adjusting agent) are particularly used.

Sunscreens, without limiting the scope of the present invention, may be selected from bemotrizinol (bis-ethylhexyloxyphenol methoxyphenyl triazine), diethylaminohydroxybenzoylhexyl benzoate, ethylhexylmethoxy cinnamate, homosalate, bisoctrizole (TINOSORB M), ethylhexyl triazone or mixtures thereof.

Actives for stimulating skin regeneration by eliminating toxins in the present invention relate to *Candida saitoana* extract; bisabolol; *Casearia sylvestris* leaf extract, and a mixture of *Casearia sylvestris*/silica or mixtures thereof.

*Candida saitoana* extract stimulates cellular detoxification mechanisms through cellular autophagy, thereby reducing the build-up of cellular toxins. Bisabolol, which may also be included in the composition, acts on the dermis and epidermis damage mechanisms by regulating the production of microdamage causative agents IL-6 and IL-8.

The following examples, without limitation, illustrate the anti-aging cosmetic compositions according to the present invention, which surprisingly act simultaneously on the six major physiological mechanisms of the skin, promoting deep nutrition combined with the antioxidative effect and the effect of elimination of toxins, particularly when they are used in the form of a system day care and night care compositions that complement each other.

EXAMPLES

Example 1. Preparation of (30+) (45+) (60+) (70+) Day Care Cosmetic Compositions Day care cosmetic compositions were produced as oil-in-water cream gel emulsions where oil is the dispersed phase and water is the continuous phase. Both phases were heated at a temperature of 75-80° C., the oily phase, where the sunscreens are, was subsequently poured onto the aqueous phase under stirring for about 10 minutes. Thereafter the cooling phase was started by adding an aqueous phase with a polymer neutralizing agent. When the temperature reached about 60° C., the sensory modifier phase (silicones) was added and when the temperature reached 40° C., preservatives, fragrance, sensory modifiers (particles) and the high temperature-sensitive agents were added.

The following table illustrates the (30+) cosmetic compositions, according to the present invention, thus produced:

TABLE 1

(30+) anti-aging, day care cosmetic compositions

| Ingredient | Example A | Example B |
|---|---|---|
| Acetyl tetrapeptide-2 and caprylyl glycol and water complex | 1.5 | 1 |
| Acrylates/$C_{10-30}$ Alkyl Acrylate Crosspolymer | 0.25 | 0.15 |
| Aluminum Starch Octenylsuccinate | 2 | 1.5 |
| Butylated Hydroxytoluene (BHT) | 0.1 | 0.1 |
| Bemotrizinol | 2.95 | 3.2 |
| *Camellia sinensis* (leaf extract) | 0.025 | 0.025 |
| Caprylyl Methicone | 1.5 | 1 |
| Cyclopentasiloxane | 9 | 9 |
| Cyclopentasiloxane (and) Dimethicone Crosspolymer | 3 | 2 |
| $C_{12-15}$ Alkyl Benzoate | 2 | 1 |
| Dibutyl Adipate | 0.5 | 0.6 |
| Dicaprylyl Carbonate | 2.5 | 2.4 |
| Diethylamino Hydroxybenzoyl Hexylbenzoate | 3 | 4.8 |
| Disodium EDTA | 0.1 | 0.1 |
| Ethylhexyl Methoxycinnamate | 9 | 13 |
| fragrance | 0.22 | 0.22 |
| Glycerin | 5 | 7.935 |
| Glyceryl Stearate Citrate | 1.5 | 0.5 |
| Homosalate | 3 | 4 |
| Iodopropynyl Butylcarbamate | 0.098 | 0.098 |
| *Murumuru* butter (crude/filtered) | 0.5 | 0.5 |
| Pataqueira essential oil | 0.001 | 0.001 |
| Phenoxyethanol | 0.8 | 0.8 |
| Potassium Cetyl Phosphate | 0.6 | 0.6 |
| Simulgel NS | 2 | 1 |
| *Spilanthes acmella* | 0.125 | 0.125 |
| *Theobroma cacao* (seed extract) | 0.01 | 0.01 |
| Tinosorb M | 2.5 | 3 |
| Tocopherol Acetate | 0.2 | 0.2 |
| Triethanolamine 99W | 0.35 | 0.5 |
| xanthan gum | 0.25 | 0.415 |
| aqua | 45.421 | 40.221 |

The following table illustrates the (45+) cosmetic compositions, according to the present invention, thus produced:

TABLE 2

(45+) anti-aging, day care cosmetic compositions

| Ingredient | Example A | Example B |
|---|---|---|
| Acetyl tetrapeptide-2 and caprylyl glycol and water complex | 1.50 | 1.50 |
| Acrylates/$C_{10-30}$ Alkyl Acrylate Crosspolymer | 0.28 | 0.20 |
| aqua | 41.90 | 35.48 |
| Butylated Hydroxytoluene (BHT) | 0.10 | 0.10 |
| Bemotrizinol | 2.95 | 2.74 |
| *Camellia sinensis* leaf extract | 0.01 | 0.01 |
| caprylyl methicone | 1.50 | 1.20 |
| Caprylic/Capric Triglyceride | 3.00 | 2.40 |
| Cyclopentasiloxane | 9.00 | 12.50 |
| $C_{12-15}$ Alkyl Benzoate | 2.00 | 2.80 |
| Diethylamino hydroxybenzoyl hexyl benzoate | 2.50 | 1.50 |
| Disodium EDTA | 0.10 | 0.12 |
| Ethylhexyl Methoxycinnamate | 9.00 | 7.80 |
| Ethylhexyl Triazone | 1.00 | 1.20 |
| Fragrance | 0.18 | 0.16 |
| Glycerin | 5.00 | 4.00 |
| Glyceryl Stearate Citrate (plant origin) | 1.50 | 2.15 |
| Homosalate | 3.00 | 4.70 |
| *Hymenaea courbaril* (leaf extract) | 0.25 | 0.41 |
| Iodopropynyl Butylcarbamate | 0.10 | 0.15 |
| Isoamyl Cocoate | 2.00 | 3.20 |
| Crude/Filtered *Murumuru* Butter | 0.50 | 0.70 |
| Nylon-12 | 1.00 | 1.50 |
| Pataqueira essential oil | 0.001 | 0.001 |
| Phenoxyethanol | 0.80 | 0.80 |
| Polymethylsilsesquioxane | 4.50 | 3.70 |
| Potassium Cetyl Phosphate | 0.60 | 0.50 |
| Simulgel NS | 2.00 | 3.20 |
| Sodium cocoyl amino acids/sarcosine/potassium aspartate/magnesium aspartate/propylene glycol and water complex | 1.50 | 2.20 |
| *Theobroma cacao* (leaf extract) | 0.01 | 0.01 |
| Tinosorb M | 1.50 | 2.00 |
| Tocopherol Acetate | 0.20 | 0.32 |
| Triethanolamine | 0.38 | 0.55 |
| Xanthan gum | 0.15 | 0.20 |

The following table illustrates the (60+) cosmetic compositions, according to the present invention, thus produced:

TABLE 3

(60+) anti-aging, day care cosmetic compositions

| Ingredient | Example A | Example B |
|---|---|---|
| Acetyl tetrapeptide-2 and caprylyl glycol and water complex | 1.50 | 2.00 |
| Acrylates/$C_{10-30}$ Alkyl Acrylate Crosspolymer | 0.30 | 0.40 |
| Water and *Paeonia albiflora* root extract/phenoxyethanol/ethylhexyl glycerin complex | 2.00 | 4.00 |
| aqua | 44.91 | 44.68 |
| Butylated Hydroxytoluene (BHT) | 0.10 | 0.12 |
| Bemotrizinol | 2.95 | 4.00 |
| *Camellia sinensis* leaf extract | 0.01 | 0.01 |
| caprylyl methicone | 1.50 | 1.20 |
| Caprylic/Capric Triglyceride | 3.00 | 2.00 |
| Cyclopentasiloxane | 8.00 | 5.00 |
| $C_{12-15}$ Alkyl Benzoate | 2.00 | 1.00 |
| Diethylamino Hydroxybenzoyl Hexyl Benzoate | 2.50 | 3.00 |
| Disodium EDTA | 0.10 | 0.15 |
| Ethylhexyl Methoxycinnamate | 9.00 | 5.00 |
| Ethylhexyl Triazone | 1.00 | 1.50 |
| Fragrance 1 | 0.20 | 0.21 |
| Fragrance 2 | 0.0010 | 0.0015 |
| Glycerin | 5.00 | 7.00 |
| Glyceryl Stearate Citrate | 1.50 | 1.20 |
| Homosalate | 3.00 | 2.00 |
| Iodopropynyl Butylcarbamate | 0.10 | 0.08 |
| Isoamyl Cocoate - TEGOSOFT AC | 2.00 | 3.20 |
| Crude/Filtered *Murumuru* Butter | 0.50 | 0.75 |
| Phenoxyethanol | 0.80 | 1.36 |
| Polymethylsilsesquioxane | 3.00 | 4.50 |
| Potassium Cetyl Phosphate | 0.60 | 0.50 |
| *Schinus terebinthifolius* (leaf extract) | 0.01 | 0.01 |
| SIMULGEL NS | 2.00 | 1.50 |
| *Theobroma cacao* (cocoa) seed extract | 0.01 | 0.01 |
| Tinosorb M | 1.50 | 2.55 |
| Tocopherol Acetate | 0.20 | 0.15 |
| Triethanolamine | 0.38 | 0.40 |
| *Casearia Sylvestris* leaf extract | 0.05 | 0.07 |
| Xanthan gum | 0.28 | 0.45 |

The following table illustrates the (70+) cosmetic compositions, according to the present invention, thus produced:

TABLE 4

(70+) anti-aging, day care cosmetic compositions

| Ingredients | Example A | Example B |
|---|---|---|
| Acetyl tetrapeptide-2 and caprylyl glycol and water complex | 0.45 | 2.55 |
| Acrylates/C$_{10-30}$ Alkyl Acrylate Crosspolymer | 0.09 | 0.51 |
| Water and *Cichorium intybus* root extract complex | 0.9 | 5.1 |
| aqua | 13.0572 | 73.9908 |
| Butylated Hydroxytoluene (BHT) | 0.03 | 0.17 |
| Bemotrizinol | 0.885 | 5.015 |
| *Camellia sinensis* leaf extract | 0.003 | 0.017 |
| caprylyl methicone | 0.45 | 2.55 |
| Caprylic/Capric Triglyceride | 0.9 | 5.1 |
| Cyclopentasiloxane | 2.4 | 13.6 |
| C$_{12-15}$ Alkyl Benzoate | 0.6 | 3.4 |
| Diethylamino Hydroxybenzoyl Hexyl Benzoate | 0.75 | 4.25 |
| Disodium EDTA | 0.03 | 0.17 |
| Ethylhexyl Methoxycinnamate | 2.7 | 15.3 |
| Ethylhexyl Triazone | 0.3 | 1.7 |
| Fragrance | 0.105 | 0.595 |
| Glycerin | 1.5 | 8.5 |
| Glyceryl Stearate Citrate | 0.45 | 2.55 |
| Homosalate | 0.9 | 5.1 |
| Iodopropynyl Butylcarbamate | 0.0294 | 0.1666 |
| Isoamyl Cocoate - TEGOSOFT AC | 0.6 | 3.4 |
| *Murumuru* butter | 0.15 | 0.85 |
| Pataqueira essential oil | 0.0009 | 0.0051 |
| Omega 6 passion fruit ceramide | 0.09 | 0.51 |
| Phenoxyethanol | 0.24 | 1.36 |
| Polymethylsilsesquioxane | 0.9 | 5.1 |
| Potassium Cetyl Phosphate | 0.18 | 1.02 |
| SIMULGEL NS | 0.6 | 3.4 |
| *Theobroma cacao* seed extract | 0.003 | 0.017 |
| TINOSORB M | 0.45 | 2.55 |
| Tocopherol Acetate | 0.06 | 0.34 |
| Triethanolamine | 0.114 | 0.646 |
| Xanthan gum | 0.0825 | 0.4675 |

Example 2. Preparation of (30+) (45+) (60+) (70+) Night Care Compositions

Night care cosmetic compositions were produced as oil-in-water cream gel emulsions where oil is the dispersed phase and water is the continuous phase. In this case, heating of the aqueous phase was started in the main container to the temperature of about 75 and about 80° C. and, with stirring, the oily phase was added under stirring for about 10 minutes. Thereafter the cooling phase was started by adding an aqueous phase with a polymer neutralizing agent. When the temperature reached about 60° C., the sensory modifier phase (silicones) was added and when the temperature reached about 40° C., preservatives, fragrance, sensory modifiers (particles) and high temperature-sensitive agents were added.

The following table illustrates the (30+) cosmetic compositions according to the present invention thus produced:

TABLE 5

(30+) anti-aging, night care cosmetic compositions

| Ingredient | Example C | Example D |
|---|---|---|
| Acetyl tetrapeptide-2 and caprylyl glycol and water complex | 2 | 3 |
| Butylated Hydroxytoluene (BHT) | 0.1 | 0.15 |
| Bisabolol | 0.5 | 0.7 |
| *Camellia sinensis* (leaf extract) | 0.025 | 0.0125 |
| Carbopol ETD 2020 | 0.25 | 0.125 |
| Cyclopentasiloxane | 6 | 10 |
| Cyclopentasiloxane (and) Dimethicone Crosspolymer | 4 | 2 |
| C$_{12-15}$ Alkyl Benzoate | 2 | 1 |
| Dicaprylyl Carbonate | 3.5 | 1.75 |
| Disodium EDTA | 0.1 | 0.05 |
| fragrance | 0.22 | 0.11 |
| Glycerin | 5 | 6.142 |
| Glyceryl stearate and PEG-100 Stearate | 1 | 0.5 |
| *Candida saitoana* (hydrolyzed extract) | 1.65 | 0.825 |
| Iodopropynyl Butylcarbamate | 0.098 | 0.049 |
| Isononyl Isononanoate | 1 | 0.5 |
| Nylon1212 (SP-10L) | 3.5 | 5 |
| Pataqueira essential oil | 0.001 | 0.0015 |
| Phenoxyethanol | 0.8 | 1.2 |
| Simulgel NS | 3 | 4.2 |
| *Spilanthes acmella* | 0.125 | 0.13 |
| *Theobroma cacao* (seed extract) | 0.01 | 0.015 |
| *Theobroma cacao* (seed butter) | 0.5 | 0.7 |
| *Theobroma grandiflorum* (seed butter) | 0.5 | 0.45 |
| Tocopherol Acetate | 0.2 | 0.31 |
| Triethanolamine 99W | 0.35 | 0.582 |
| Xanthan gum | 0.25 | 0.345 |
| aqua | 63.321 | 60.153 |

The following table illustrates the (45+) cosmetic compositions according to the present invention thus produced:

TABLE 6

(45+) anti-aging, night care cosmetic compositions

| Ingredient | Example C | Example D |
|---|---|---|
| Acetyl tetrapeptide-2 and caprylyl glycol and water complex | 2.00 | 3.20 |
| aqua | 64.291 | 58.991 |
| Butylated Hydroxytoluene (BHT) | 0.10 | 0.05 |
| Bisabolol | 0.50 | 0.43 |
| Carbopol ETD 2020 | 0.25 | 0.37 |
| Cetearyl Alcohol | 1.00 | 0.60 |
| Cyclopentasiloxane | 4.00 | 4.80 |
| Cyclopentasiloxane (and) Dimethicone Crosspolymer | 4.00 | 5.70 |
| C$_{12-15}$ Alkyl Benzoate | 2.00 | 3.00 |
| Dicaprylyl Carbonate | 3.50 | 4.50 |
| Disodium EDTA | 0.10 | 0.10 |
| Fragrance | 0.20 | 0.20 |
| Glycerin | 5.00 | 5.00 |
| Glyceryl stearate and PEG-100 Stearate - plant origin | 1.20 | 1.20 |
| Hydrolyzed *Candida saitoana* extract | 1.65 | 1.65 |
| *Hymenaea courbaril* (leaf extract) | 0.25 | 0.25 |
| Iodopropynyl Butylcarbamate | 0.098 | 0.098 |
| Isononyl Isononanoate | 1.00 | 1.00 |
| Nylon 12 | 3.00 | 3.00 |
| Pataqueira essential oil | 0.001 | 0.001 |
| Phenoxyethanol | 0.80 | 0.80 |
| Simulgel NS | 2.00 | 2.00 |
| Sodium cocoyl amino acids/sarcosine/potassium aspartate/magnesium aspartate/propylene glycol and water complex | 1.50 | 1.50 |
| *Theobroma cacao* seed extract | 0.01 | 0.01 |
| *Theobroma cacao* seed butter | 0.50 | 0.50 |
| *Theobroma grandiflorum* seed butter | 0.50 | 0.50 |
| Tocopherol Acetate | 0.20 | 0.20 |
| Triethanolamine | 0.35 | 0.35 |

The following table illustrates the (60+) cosmetic compositions according to the present invention thus produced:

TABLE 7

(60+) anti-aging, night care cosmetic compositions

| Ingredient | Example C | Example D |
|---|---|---|
| Acetyl tetrapeptide-2 and caprylyl glycol and water complex | 2.00 | 1.50 |
| Water and *Paeoniaal biflora* root extract/phenoxyethanol/ethylhexyl glycerin complex | 2.00 | 1.50 |
| aqua | 64.98 | 62.22 |
| Butylated Hydroxytoluene (BHT) | 0.10 | 0.05 |
| Bisabolol | 0.50 | 0.40 |
| Carbopol ETD 2020 | 0.25 | 0.35 |
| Cetearyl Alcohol | 1.25 | 1.50 |
| Cyclopentasiloxane | 4.00 | 6.00 |
| Cyclopentasiloxane (and) Dimethicone Crosspolymer | 4.00 | 6.50 |
| Dicaprylyl Carbonate | 1.00 | 1.50 |
| Disodium EDTA | 0.10 | 0.12 |
| Ethyl Macadamate | 3.00 | 4.00 |
| Fragrance | 0.20 | 0.15 |
| Glycerin | 8.00 | 5.00 |
| Glyceryl Stearate and PEG-100 | 1.20 | 1.00 |
| Hydrolyzed *Candida saitoana* extract | 1.65 | 1.20 |
| Iodopropynyl Butylcarbamate | 0.10 | 0.05 |
| Isononyl Isononanoate | 1.00 | 1.50 |
| Pataqueira essential oil | 0.0010 | 0.0015 |
| Phenoxyethanol | 0.80 | 1.20 |
| *Schinus terebinthifolius* (leaf extract) | 0.01 | 0.01 |
| SIMULGEL NS | 2.00 | 2.50 |
| *Theobroma cacao* (leaf extract) | 0.01 | 0.01 |
| *Theobroma cacao* seed butter | 0.50 | 0.30 |
| *Theobroma grandiflorum* seed butter | 0.50 | 0.40 |
| Tocopherol Acetate | 0.20 | 0.15 |
| Triethanolamine | 0.35 | 0.50 |
| Complex of water and a mixture of *Casearia Sylvestris* leaf extract and Silica | 0.05 | 0.04 |
| Xanthan gum | 0.25 | 0.35 |

The following table illustrates the (70+) cosmetic compositions according to the present invention thus produced:

TABLE 8

(70+) anti-aging, night care cosmetic compositions

| Ingredient | Example C | Example D |
|---|---|---|
| Acetyl tetrapeptide-2 and caprylyl glycol and water complex | 2.00 | 3.20 |
| Water and *Cichorium intybus* root extract complex | 3.00 | 3.50 |
| aqua | 62.94 | 53.94 |
| Butylated Hydroxytoluene (BHT) | 0.10 | 0.12 |
| Bisabolol | 0.50 | 0.75 |
| Carbopol ETD 2020 | 0.25 | 0.30 |
| Cetearyl Alcohol | 2.00 | 2.80 |
| Cyclopentasiloxane | 4.00 | 5.80 |
| Cyclopentasiloxane (and) Dimethicone Crosspolymer | 4.00 | 3.00 |
| Dicaprylyl Carbonate | 1.00 | 1.20 |
| Disodium EDTA | 0.10 | 0.15 |
| Ethyl Macadamate | 3.00 | 3.50 |
| Fragrance | 0.25 | 0.28 |
| Glycerin | 8.00 | 9.70 |
| Glyceryl Stearate and PEG-100 | 1.20 | 1.10 |
| Hydrolyzed *Candida saitoana* extract | 1.65 | 1.7800 |
| Iodopropynyl Butylcarbamate | 0.10 | 0.13 |
| Isononyl Isononanoate | 1.00 | 1.50 |
| Pataqueira essential oil | 0.00 | 0.0014 |
| Omega 6 passion fruit ceramide | 0.30 | 0.42 |
| Phenoxyethanol | 0.80 | 1.24 |
| SIMULGEL NS | 2.00 | 3.20 |
| *Theobroma cacao* seed extract | 0.01 | 0.0150 |
| *Theobroma cacao* seed butter | 0.50 | 0.65 |
| *Theobroma grandiflorum* seed butter | 0.50 | 0.85 |
| Tocopherol Acetate | 0.20 | 0.25 |
| Triethanolamine | 0.35 | 0.42 |
| Xanthan gum | 0.25 | 0.20 |

Example 3. Evaluation of Skin Hydration by Corneometry—Compositions (30+)

Volunteers have been recruited for an evaluation of the hydration effect of cosmetic compositions according to example 1 of the present invention. Twenty-one (21) survey participants have completed the study and there were no reports or evidence of adverse reaction during the study.

The survey participants were asked to discontinue the use of any cosmetic product on their forearms up to 48 hours prior to the beginning of the study.

For the evaluation two 2.5×4.0 cm sites were marked on the volar forearm of the survey participant, wherein one site was used as control (without any products being applied). After the baseline corneometry measurements (performed on Corneometer® 825 and Multiprobe Adapter MPA-5, CKeletronics, Germany), the formulations according to example 1 were applied and the survey participants remained in the lab for additional measurements to be taken after 15 minutes, 4.6, 8 and 12 hours.

After the 12-hour measurement the survey participants were sent home, being instructed not to wet or wash their arms. The next day they returned to the lab for another measurement to be taken 24 hours after application.

Application of the compositions according to example 1 of the present invention was found to maintain the skin hydrated for up to 24 hours as compared to control (skin without any products being applied). Application of the compositions according to example 1 of the present invention increased the skin hydration level by up to 62%. All the participants presented an improvement in skin hydration.

Example 4. Evaluation of the Anti-Aging Efficacy of (30+) Day Care Compositions Through Instrumental Measurements Under Normal Use Conditions A study was carried out to ascertain the efficacy of the formulations of Example 1 according to the present invention in reducing wrinkles and improving skin texture.

The volunteers rested in a temperature- and moisture-controlled room for 30 minutes before the baseline measurements and during the interval between measurements. Application was made once a day on the face and neck evenly after cleansing the skin.

On the first day, after 14 days, and after 28 days, 7 consecutive images of the periorbital region were obtained using Optical 3D Skin Measuring Device PRIMOS Compact 5.075 for evaluation of wrinkles/texture on one side of the face and 3 (front and side) images using Visia CR (Canfield Scientific, Inc.) that were used for registration purposes.

Analysis of the obtained images allowed us to conclude that the compositions according to example 1 of the present invention caused a reduction in the wrinkle volume, a reduction in the average depth of the wrinkles and a reduction in the maximum roughness of the wrinkles after fourteen days of use.

Example 5. Evaluation of the Anti-Aging Efficacy of (30+) Night Care Cosmetic Compositions Through Instrumental Measurements Under Normal Use Conditions The cosmetic compositions evaluated herein are according to Example 2 of the present invention, the methodology used is the same as Example 4, except for the fact that measurements were taken on the first day, after 14 days, after 28 days and after 56 days.

Analysis of the obtained images allowed us to conclude that the cosmetic compositions according to example 2 of the present invention caused a reduction in wrinkle volume, a reduction in the average depth of the wrinkles and an improvement in skin undulation after fifty-six days of use.

Example 6

Evaluation of the Skin Barrier Fortifying Effect Provided by the Use of (30+) Day Care Cosmetic Compositions A study was carried out to assess the effect of the compositions according to example 1 of the present invention on the fortification of the skin barrier.

Volunteers were instructed to discontinue the use of any topical products on their forearms for 48 hours prior to the beginning of the study.

The methodology consisted of assessing the transepidermal water loss from the skin after a process of partially removing the corneous extract. Measurements were collected in the beginning of the study and after 7, 14 and 28 days of use of the compositions according to example 1 of the present invention.

A tape-stripping process was used to assess the effect of fortification of the skin barrier, where a transparent medical adhesive tape was applied and removed 30 times repeatedly on sites marked on the volar forearm, followed by measuring the transepidermal water loss (Tewameter® 300 and Multiprobe Adapter MPA-5, CKeletronics, Germany). Application of the compositions is made on only one forearm, causing the other to be the control, that is, no topical products are applied thereto.

From the crude TEWL (trans epidermal water loss) values, designated E, the variation in transepidermal water loss was calculated as a function of the removal of stratum corneum layers ($\Delta E$).

$$\Delta Ei, X = ET30, X - ET0, X$$

wherein: $\Delta E$=Variation in transepidermal water loss from the skin; i=0, 7, 14 or 28 days. ET30=TEWL value after 30 removals of stratum corneum layers. ET0=TEWL value measured on whole skin; X=control or formulation used.

Analysis of the results is shown in the graph shown in FIG. 1.

The obtained results allow us to conclude that the formulations had a significant effect on skin barrier fortification as compared to control after 14 and 28 days of home use.

Example 7. Evaluation of the Skin Barrier Fortifying Effect Provided by the Use of (30+) Night Care Compositions The formulations to be evaluated are in accordance with Example 2 of the present invention, the methodology employed is the same as Example 6. Measurements and calculations were performed similarly to the previous example.

Figure 2:
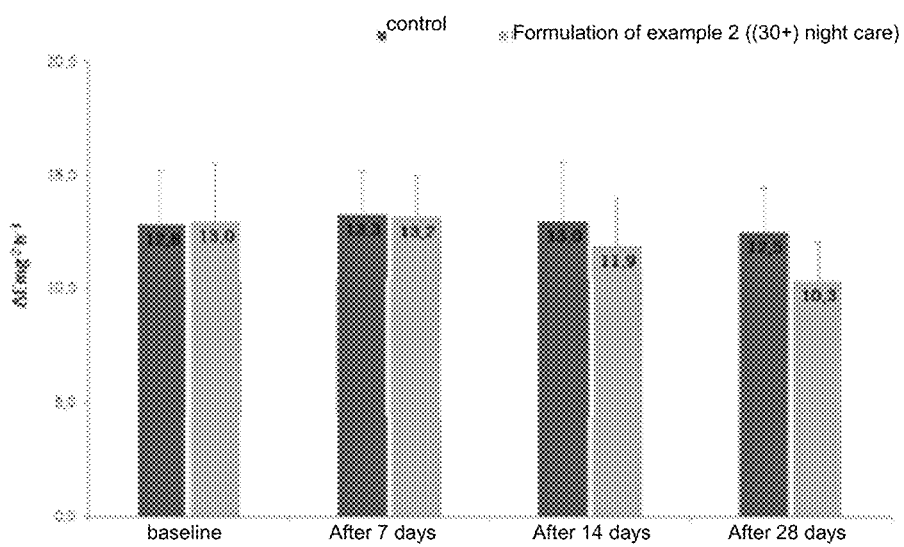
FIG. 2 shows a graph of the average variation in transepidermal water loss from skin obtained in the beginning of the study and after 7, 14 and 28 days of use of the (30+) compositions according to example 2 (night care) over the control.

Analysis of the results is shown in the graph shown in FIG. 2.

The obtained results allow us to conclude that the formulations had a significant effect on skin barrier fortification as compared to control after 14 and 28 days of home use.

Example 8. Evaluation of the Anti-Aging Efficacy of a (45+) Night Care Cosmetic Product Through Instrumental Measurements Under Normal Use Conditions The aim of the study was to ascertain the efficacy of compositions according to the present invention in reducing wrinkles and improving skin texture when applied once a day by instrumental evaluations after 14±2 days, 28±2 days and 56±2 days of use.

35 female participants aged 46 to 59 years, average age of 53 years, phototypes I to IV, having wrinkles or expression lines on the periorbital region and of all skin types were evaluated by a dermatologist in the beginning and in the end of the research. The survey participants rested in a temperature- and moisture-controlled room for 30 minutes before the baseline measurements and during the interval between measurements. On D0, D14, D28 and D56, 7 consecutive images of the periorbital region were obtained using Optical 3D Skin Measuring Device PRIMOS Compact 5.075 for evaluating wrinkles/texture on one side of the face and 3 (front and side) images using Visia CR (Canfield Scientific, Inc.) that were used for registration purposes.

According to the methodology used to assess efficacy, it was concluded that relatively to the baseline (D0):

there was a reduction in wrinkle volume after twenty-eight days of use;

there was a reduction in the average roughness of the wrinkles after fourteen, twenty-eight and fifty-six days of use;

there was a reduction in the average depth of the wrinkles after fourteen and fifty-six days of use;

there was a reduction in wrinkle roughness after fourteen and fifty-six days of use;

there was an improvement in skin texture after fifty-six days of use.

Figure 3:
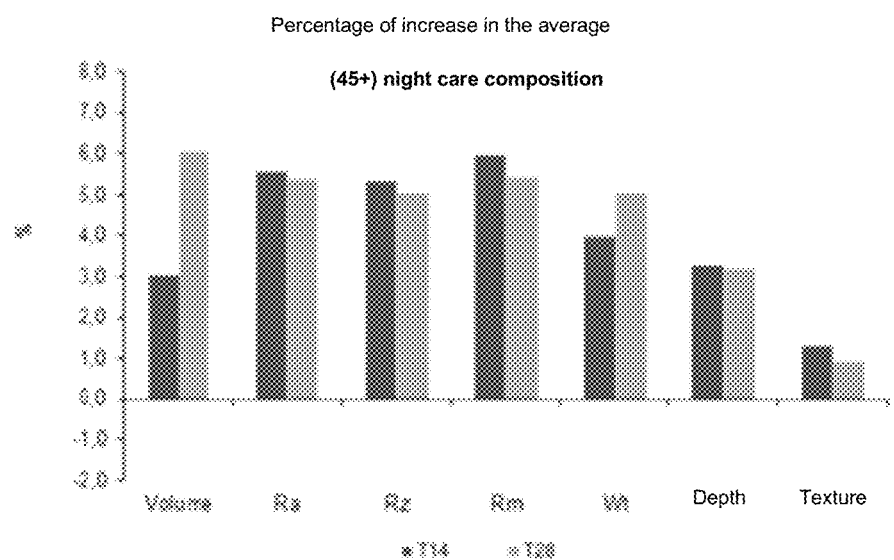
FIGS. 3 and 4 show the average improvement in tests carried out according to example 8 of the present specification for (45+) night care compositions.
Figure 4:
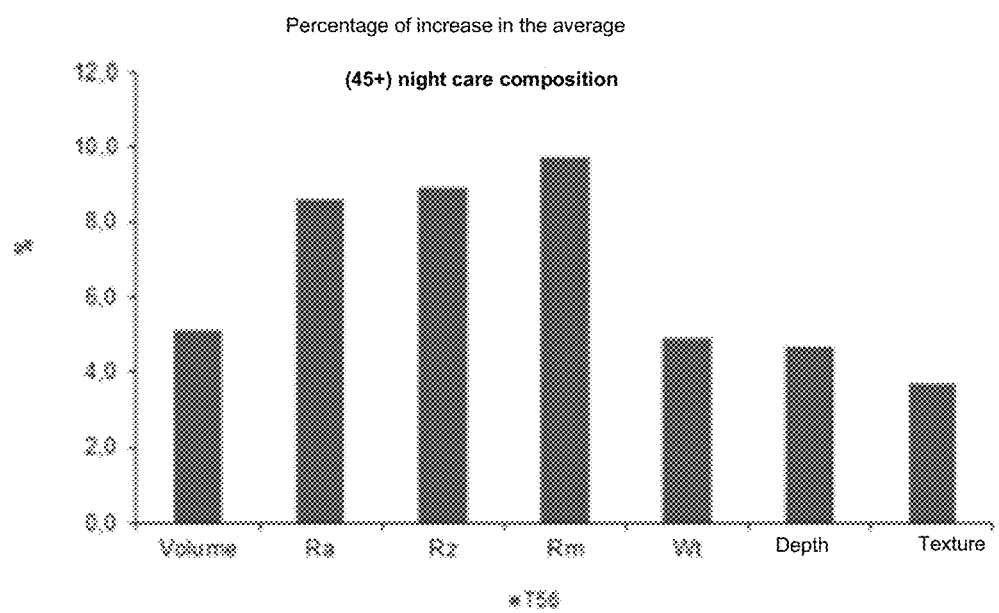

FIGS. 3 and 4 show the above results.

Example 9. Efficacy Test—Clinical Trial Evaluating the Efficacy of (45+) Day Care Compositions in Reducing Signs of Facial Aging Efficacy of the compositions according to the present invention in reducing signs of facial aging such as wrinkles and sagging was evaluated by means of clinical and subjective evaluations performed on 69 volunteers who applied the compositions once a day on the face and neck, evenly after cleansing the skin.

It was a single-center, non-comparative, non-randomized study intended to assess the clinical efficacy in reducing the signs of facial aging of a cosmetic product evaluated on the indicated site according to the mode of use for 28 days. Clinical assessments were performed on Visits: Visit 01/D-7, Visit 02/D0, Visit 03/D07, Visit 04/D14, Visit 05/D28 and Visit 06/D56 after 56 days of use of the compositions.

Clinical evaluation times were: D-7 (start of wash out); D0 (prior to the use of the product and after the wash-out period) D7 (after 7 days of use of the product), D14

(fourteen days of use of the product), D28 (twenty-eight days of use of the product) and D56 (fifty-six days of use of the product). Subjective evaluations were also performed on the visits.

Clinical assessment has shown that:

The compositions according to the present invention provided an improvement in the facial contour at all evaluated times, being statistically significant ($p \leq 0.05$) at D56 as compared to the baseline D0;

The compositions according to the present invention provided an improvement in the healthy appearance of the skin of volunteers at all evaluated times, being statistically significant ($p \leq 0.05$) as compared to the baseline D0;

The compositions according to the present invention provided an improvement in the general appearance of the skin of volunteers at all evaluated times, being statistically significant ($p \leq 0.05$) at D14 and D56 as compared to the baseline D0;

In the subjective assessment:

There was an improvement in facial harmony (improvement in the facial contour) of the volunteers' skin at all evaluated times, also being statistically significant ($p \leq 0.05$);

There was an improvement in the general appearance of the skin (bright, revitalized, rebalanced, healthy looking skin) of the volunteers at all evaluated times, also being statistically significant ($p \leq 0.05$);

It was observed that at least 82% of the volunteers reported that facial harmony and overall skin appearance were improved or were greatly improved after using the composition.

Example 10. Efficacy Test—Clinical Trial Evaluating the Efficacy of (45+) Night Care Compositions in Reducing Signs of Facial Aging Efficacy of the compositions according to the present invention in reducing signs of facial aging such as wrinkles and sagging was evaluated by means of clinical and subjective assessments performed on 72 volunteers who used the compositions on a daily basis by evenly applying it on the face overnight after cleansing the skin.

It was a single-center, non-comparative, non-randomized study intended to assess the clinical efficacy in reducing the signs of facial aging of the product evaluated on the indicated site according to the mode of use for 28 days. Clinical assessments were performed on Visits: Visit 01/D-7, Visit 02/D0, Visit 03/D07, Visit 04/D14, Visit 05/D28 and Visit 06/D56 after 56 days of use of the compositions.

Clinical evaluation times were: D-7 (start of wash out); D0 (prior to the use of the product and after the wash-out period) D7 (after 7 days of use of the product), D14 (fourteen days of use of the product), D28 (twenty-eight days of use of the product) and D56 (fifty-six days of use of the product). Subjective evaluations were also performed on the visits.

Clinical assessment has shown that:

The compositions according to the present invention provided an improvement in the degree of periorbital wrinkles at D14, D28 and D56 but they were not statistically significant ($p > 0.05$);

The compositions according to the present invention provided an improvement in the facial contour at all evaluated times, being statistically significant ($p \leq 0.05$) at D56 as compared to the baseline D0;

The compositions according to the present invention provided an improvement in the healthy appearance of the skin of volunteers at all evaluated times, being statistically significant ($p \leq 0.05$) at D14, D28 and D56 as compared to the baseline D0;

The compositions according to the present invention provided an improvement in the general appearance of the skin of volunteers at all evaluated times, being statistically significant ($p \leq 0.05$) as compared to the baseline D0;

In the subjective assessment:

There was an improvement in facial harmony (improvement in the facial contour) of the volunteers' skin at all evaluated times, also being statistically significant ($p \leq 0.05$);

There was an improvement in the overall skin appearance (bright, revitalized, rebalanced, healthy looking skin) of the volunteers at all evaluated times, also being statistically significant ($p \leq 0.05$);

It was observed that at least 70% and 78% of the volunteers reported that facial harmony and overall skin appearance were improved or were greatly improved, respectively, after using the composition; also being statistically significant ($p \leq 0.05$);

Example 11. Evaluation of the Increase in Skin Firmness and Elasticity by Cutometry for (45+) Day Care Compositions The methodology consisted of evaluating the increase in skin firmness and elasticity through cutometry (Cutometer® MPA-580 and Multiprobe Adapter MPA-580, CKeletronics, Germany) performed in the beginning of the study and after 28 days of home use of the composition under investigation. The increase in skin firmness has been evaluated using the Ur/Ue parameter (R5) and the increase in skin elasticity was evaluated using the Ur/Uf parameter (R7). Cutometry measurements were performed on the forearm region and the outer corner of the eye.

25 survey participants have completed the study and their average age was: 53±4 years, who applied the product on a daily basis once during daytime on the face and forearm by spreading it evenly after cleansing the skin.

Skin firmness has been assessed using the Ur/Ue parameter. Ur/Ue parameter is the ratio between immediate retraction and immediate skin deformation and corresponds to the biological elasticity.

Increased skin firmness is evidenced by an increase in the Ur/Ue parameter that reflects an improvement of properties of the elastic fibers and collagen.

Skin elasticity was evaluated using the Ur/Uf parameter, which consists of the ratio between immediate retraction and total skin deformation, including the viscous part of skin deformation, and corresponds to biological elasticity.

Increased skin elasticity is evidenced by the increase in the Ur/Uf parameter that reflects the an improvement of the elastic fiber properties.

Based on the mean values of the Ur/Ue parameter, the percent increase in skin firmness (% AF) is calculated according to equation 1.

$$\%AFti = 100 * (Ur/Ueti - Ur/Uet0)/Ur/Uet0 \quad \text{(equation 1)}$$

wherein:

% AFti=percent increase in firmness;

Ur/Ueti=mean values of the Ur/Ue parameter obtained after i days of study (i=28 days);

Ur/Urt0=mean values of the Ur/Ue parameter obtained in the beginning of the study (baseline).

Based on the mean values of the Ur/Uf parameter, the percent increase in skin elasticity (% AE) is calculated according to equation 2.

$$\%AEti=100*(Ur/Ufti-Ur/Uft0)/Ur/Uft0 \quad \text{(equation 2)}$$

wherein:
% AEti=percent increase in elasticity;
Ur/Ufti=mean values of the Ur/Uf parameter obtained after i days of study (i=28 days);
Ur/Uft0=mean values of the Ur/Uf parameter obtained in the beginning of the study (baseline).

According to the obtained results it could ne noted that:
There was a significant increase in skin firmness on the facial region after 28 days of home use. This result was evidenced by the significant increase in the Ur/Ue parameter.
It was found that the compositions according to the present invention provided a 36.7% average increase in facial skin firmness after 28 days of home use as compared to the baseline skin condition.
68% of the survey participants exhibited an increased facial skin firmness, as evidenced by an increase in the Ur/Ue parameter after 28 days of home use of the compositions according to the present invention.

There was a significant increase in skin firmness and elasticity on the volar forearm region after 28 days of home use. These results were evidenced by the significant increase in Ur/Ue and Ur/Uf parameters, respectively.

The Ur/Ue parameter has shown that application of the compositions according to the present invention provided a 13.0% average increase in skin firmness on the forearm region and the Ur/Uf parameter has shown that application of the composition provided a 6.1% average increase in skin elasticity on the forearm region after 28 days of home use as compared to the baseline skin condition.

72% of the survey participants exhibited increased forearm skin firmness, as evidenced by an increase in the Ur/Ue parameter after 28 days of home use of the composition being investigated.

76% of the survey participants exhibited increased forearm skin elasticity, as evidenced.

Figure 5:
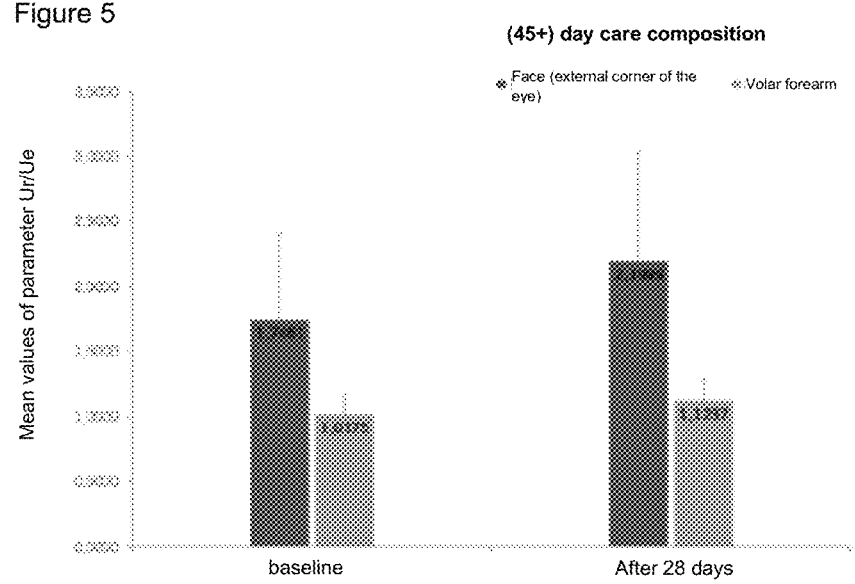
FIG. 5 shows the mean values of the Ur/Ue parameter obtained in the beginning of the study and after 28 days of home use (mean±SD, n=25) for (45+) day care compositions.
Figure 6:
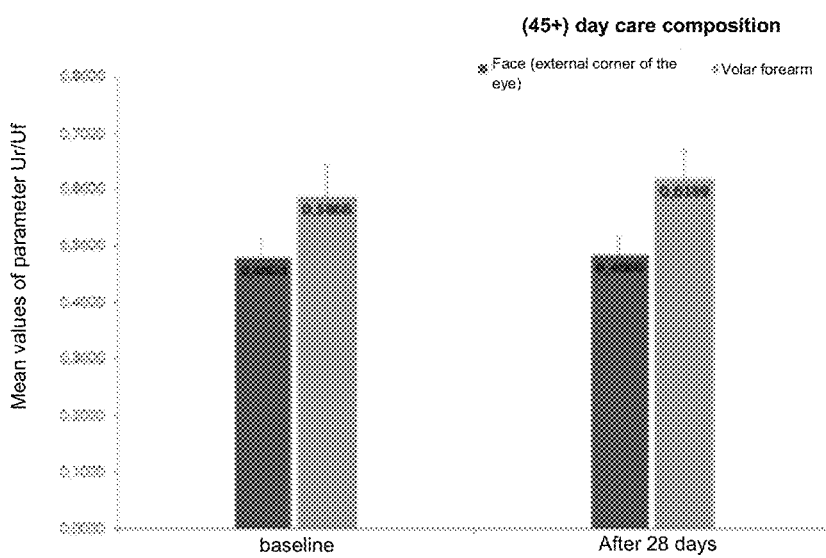
FIG. 6 depicts the mean values of the Ur/Uf parameter obtained in the face and forearm regions in the beginning of the study and after 28 days of home use for (45+) day care compositions.
Figure 7:
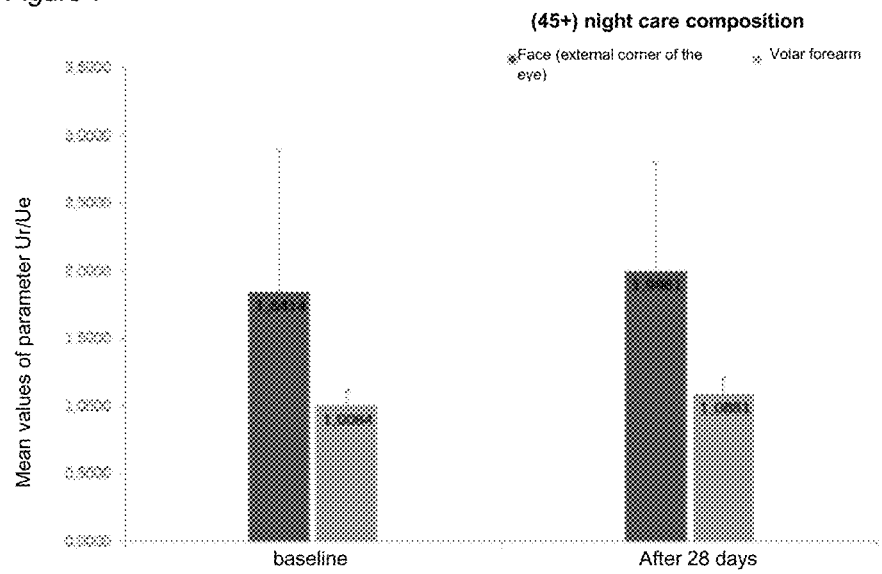
FIG. 7 depicts the mean values of Ur/Ue parameter obtained in the beginning of the study and after 28 days of home use (mean±SD, n=23) for (45+) night care compositions.
Figure 8:
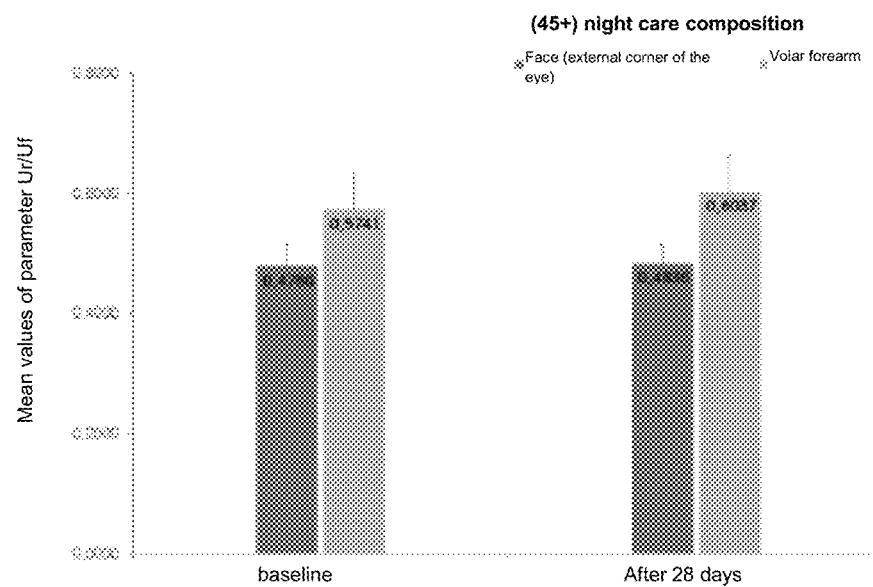
FIG. 8 shows the mean values of the Ur/Uf parameter obtained in the beginning of the study and after 28 days of home use (mean±SD, n=23) for (45+) night care compositions.
Figure 9:
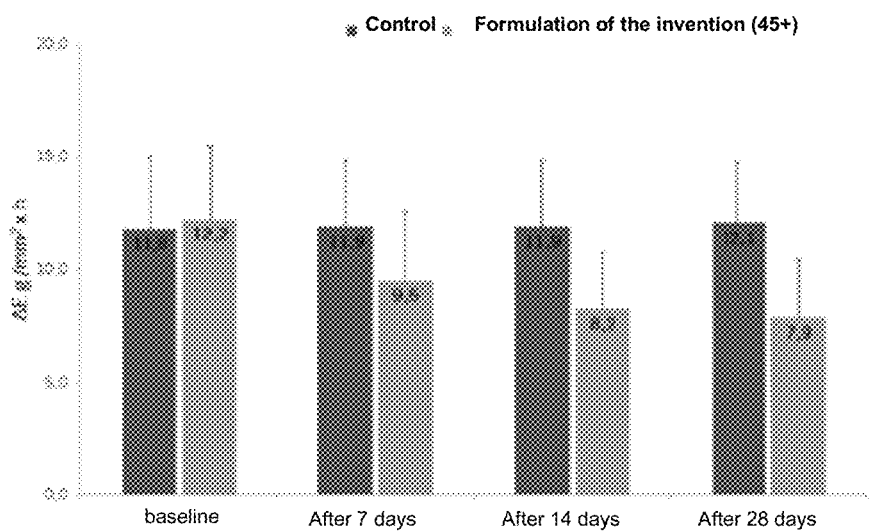
FIG. 9 shows the average variation in transepidermal water loss from the skin obtained in the beginning of the study and after 7, 14 and 28 days of use of the (45+) composition over control (Mean±SD, n=26).

FIG. 5 illustrates the mean values of the Ur/Ue parameter obtained in facial and forearm regions in the beginning of the study and after 28 days of home use of the compositions of the present invention.

Example 12. Evaluation of the Increase in Skin Firmness and Elasticity by Cutometry for (45+) Night Care Compositions The increase in firmness and elasticity of the skin after 28 days of home use of the compositions according to the present invention was evaluated.

The methodology consisted of evaluating the increase in skin firmness and elasticity through cutometry (Cutometer® MPA-580 and Multiprobe Adapter MPA-580, CKeletronics, Germany) performed in the beginning of the study and after 28 days of home use of the composition under investigation. The increase in skin firmness has been evaluated using the Ur/Ue parameter (R5) and the increase in skin elasticity was evaluated using the Ur/Uf parameter (R7). Cutometry measurements were performed on the forearm region and on the outer corner of the eye after applying the compositions according to the present invention on a daily basis once during the night-time on the face and forearm by evenly spreading it after cleansing the skin.

There was no significant increase in skin firmness and elasticity in the facial region after 28 days of home use. However, 61% of the survey participants exhibited increased skin firmness and 57% exhibited increased skin elasticity after 28 days of home use of the compositions according to the present invention.

There was a significant increase in skin firmness and elasticity on the volar forearm region after 28 days of home use. These results were evidenced by the significant increase in Ur/Eu and Ur/Uf parameters, respectively.

The Ur/Ue parameter has shown that application of the compositions according to the present invention provided a 8.9% average increase in skin firmness on the forearm region and the Ur/Uf parameter has shown that application of the compositions according to the present invention provided a 5.7% average increase in skin elasticity on the forearm region after 28 days of home use as compared to the baseline skin condition.

78% of the survey participants exhibited increased forearm skin firmness, as evidenced by an increased Ur/Ue parameter after 28 days of home use of the composition being investigated.

74% of the survey participants exhibited increased forearm skin elasticity, as evidenced by an increased Ur/Uf parameter after 28 days of home use of the composition being investigated.

Example 13. Evaluation of the Skin Barrier Fortifying Effect Provided by the Use of (45+) Cosmetic Product The skin barrier fortifying effect provided by the continuous use of the cosmetic product is evidenced by a reduced water loss observed even after removal of stratum corneum layers, exposing the innermost layers of the skin.

Assessment of skin barrier fortification was performed after 7, 14 and 28 days of home use of the compositions according to the present invention. [0136]26 female survey participants have completed the study and their average age was: 42±10 years.)

Upon enrollment of the participants in the study, they were instructed to discontinue the use of any topical products on their forearms for 48 hours prior to the beginning of the study.

The methodology consisted of assessing the transepidermal water loss from the skin after a process of partial removal of the corneous extract in the beginning of the study and after 7, 14 and 28 days of use of the composition. A tape-stripping process was used to assess the skin barrier fortifying effect, where a transparent medical adhesive tape (Transore 3M, 3M, Brazil) was applied and removed 30 times repeatedly on sites marked on the volar forearm, followed by measuring the transepidermal water loss (Tewameter® 300 and Multiprobe Adapter MPA-5, CKeletronics, Germany). The forearm on which the composition was applied and the control one were randomly selected. One forearm, which was identified with a satin ribbon bracelet, was used for application of the composition, while the other forearm remained as control (without the application of any products).

The compositions according to the present invention were applied in a sufficient amount to the forearm with the satin ribbon bracelet wrapped around the wrist. The product was applied on the clean forearm once a day at any time.

According to the achieved results, the compositions according to the present invention applied to the volar forearm skin provided a significant effect of skin barrier fortification as compared to the control after 7, 14 and 28 days of home use. The percent value of skin barrier fortification over the baseline skin condition and the control was 22.5% after 7 days, 32.2% after 14 days and 37.3% after 28 days of home use. 100.0% of the survey participants exhibited fortification of the skin barrier after home use of the investigated composition.

According to the study protocol and procedures used to assess the skin barrier fortifying effect provided by applying the compositions according to the invention to the forearm skin, it has been found that:

it has provided a significant skin barrier fortification effect as compared to the control (skin with no products applied) after 7, 14 and 28 days of home use.

the percent values of skin barrier fortification achieved over the baseline skin condition and control were: 22.5% after 7 days, 32.2% after 14 days and 37.3% after 28 days of home use.

100.0% of the survey participants exhibited fortification of the skin barrier after home use of the investigated composition.

Example 14. Evaluation of Skin Hydration by Corneometry—Compositions (45+)

Skin hydration after application of the compositions according to the present invention was assessed.

21 survey participants have completed the study and their average age was: 45±12 years.) Upon enrollment of the participants in the study, they were asked to discontinue the use of any cosmetic products on their forearms up to 48 hours prior to the beginning of the study.

For the evaluation two 2.5×4.0 cm sites were marked on the volar forearm of the survey participants, wherein one site was used as control (without any products being applied). After the baseline corneometry measurements (Corneometer® 825 and Multiprobe Adapter MPA-5, CKeletronics, Germany), the composition was applied and the survey participants remained in the lab for additional measurements to be taken after 15 minutes, 4, 6, 8 and 12 hours. After the 12-hour measurement the survey participants were sent home, being instructed not to wet or wash their arms. The next day they returned to the lab for another measurement to be taken 24 hours after application of the composition.

According to the results obtained, it could be noted that application of the compositions according to the present invention kept the skin hydrated for up to 24 hours as compared to the control (skin without any products applied). Application of the compositions according to the present invention increased the skin hydration level by up to 53%. 100% of the participants presented an improvement in skin hydration.

Capacitance measurements were performed using the Corneometer® 825 probe coupled to Multi Probe Adapter, MPA 5 (CKeletronics, Germany).

Concomitantly with the measurements, an automated Microsoft® Office Excel 2010 software sheet was used to calculate the coefficient of variation (CV) of the obtained readings. A minimum of 5 and a maximum of 10 measurements were performed per site at each evaluation time. If the CV had a value of less than 6% over 5 measurements, no more measurements were taken at the site. Otherwise, the readings were continued until a CV of less than 6% was obtained considering a maximum of 10 measurements. At the end of 10 measurements, if CV<6% was not achieved, the value of 10% is considered as a new limit to terminate the readings at the site or to restart the entire process if above 10%.

Skin hydration provided by applying a moisturizing product can be evidenced by an increase in the capacitance value generated in the capacitor formed between the base of the Corneometer® probe and the skin. The higher the capacitance value, the greater the amount of water in the skin, and therefore the higher its hydration level.

From the capacitance values (h) the difference in skin hydration ($\Delta h$) was calculated, that is, the variation in the capacitance measurements obtained at each evaluation time over the baseline measurements. The $\Delta h$ parameter was calculated for the composition and the control, according to equation 1.

$$\Delta h = hti - ht0 \quad \text{(Equation 1)}$$

From the hydration difference ($\Delta h$) values, the parameters of hydration (H) and percentage of skin hydration (% H) provided by the composition were calculated according to Equations 2 and 3.

$$Hti = \Delta hti(\text{investigated composition}) - \Delta hti(\text{control}) \quad \text{(equation 2)}$$

Equation 2. Calculation of skin hydration provided by applying the composition.

wherein: Hti=skin hydration after i hours from application of the composition;

$\Delta hti$ (control) and $\Delta hti$ (composition)=differences in skin hydration obtained for the control and the composition, respectively.

$$\%Hti = (Hti \times 100)/ht0 \quad \text{(equation 3)}$$

wherein: % Hti=hydration percentage;

Hti=skin hydration provided by applying the composition after i hours from application;

ht0=mean of the capacitance measurements obtained in the beginning of the study (baseline).

Figure 10:
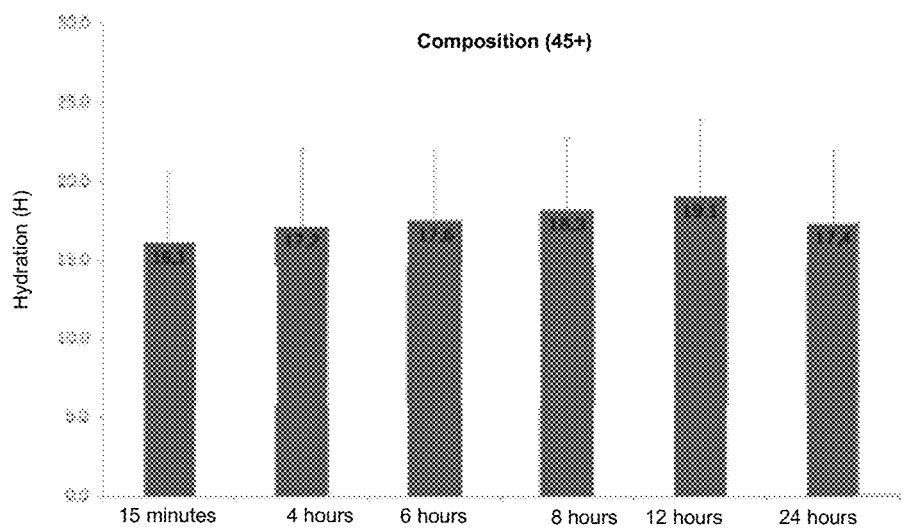
FIG. 10 shows the hydration kinetics of product (45+) according to the present invention as compared to the control.
Figure 11:
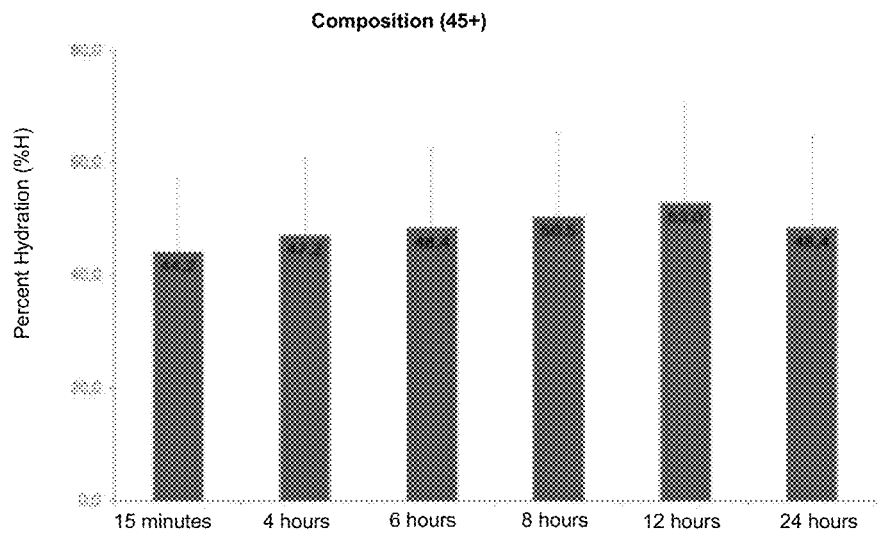
FIG. 11 shows the kinetics of the percentage of hydration given by composition (45+) relative to control.

FIGS. 10 and 11 show the mean hydration values (Hti) and the skin hydration percentage (% Hti) conferred by the application of the composition as compared to the control.

According to the study protocol and procedures used to assess skin hydration, it has been found that application of the compositions of the present invention on the forearm skin:

conferred significantly higher hydration after 15 minutes, 4, 6, 8, 12 and 24 hours from application as compared to control (skin without any products applied). This is an evidence that the investigated composition moisturized the skin.

kept the skin moisturized for up to 24 hours after application.

increased the skin hydration level by up to 53%.

100% of the survey participants exhibited increased skin hydration after applying the composition.

Example 15. Sensory Analysis to Perceived Efficacy after Application of the (60+) Day Care Cosmetic Compositions According to the Present Invention Sensory analysis was used to assess the perceived efficacy of the cosmetic compositions according to the present invention.

To that end, 40 survey participants have completed the study and their average age was: 64±3 years; Phototype (Fitzpatrick) 2.5% phototype II, 72.5% phototype III and 25.0% phototype IV.

The methodology consisted of a sensory analysis to perceived efficacy through the application of a questionnaire to be answered by the survey participants of the research after 10 minutes from the application of the composition.

After application it was shown that: 100.0% of the survey participants considered that the composition has light texture, leaves the skin soft and healthy looking; 97.5% of the survey participants considered that the composition provides natural brightness and luminosity to the skin, noticed that the composition leaves an even, homogeneous and smooth skin texture providing a peach skin feel; 95.0% of the survey participants found that the composition does not leave the skin oily and provides natural radiance to the skin; 92.5% of the survey participants perceived that the composition revitalizes the skin (reduces the appearance of tired skin); 87.5% of the survey participants perceived that the composition recovers the natural radiance of the skin; 82.5% of the survey participants perceived that the composition immediately disguises fine expression lines and wrinkles; 80.0% of the survey participants perceived that the composition provides a an immediate firmness feel to the skin (immediate tensor effect).

Example 16. Sensory Analysis to Perceived Efficacy after Application of the (60+) Night Care Cosmetic Compositions According to the Present Invention Sensory analysis was used to assess the perceived efficacy of the cosmetic compositions according to the present invention.

40 survey participants have completed the study and their average age was: 64±3 years; Phototype (Fitzpatrick) 5.0% phototype II, 85.0% phototype III and 10.0% phototype IV.

The methodology consisted of a sensory analysis to perceived efficacy through the application of a questionnaire to be answered by the survey participants of the research after 10 minutes from the application of the composition.

After application it was shown that: 100.0% of the survey participants considered that the composition has light texture and provides natural luminosity to the skin; 97.5% of the survey participants considered that the composition provides natural brightness to the skin; 95.0% of the survey participants perceived that the composition leaves the skin soft and smooth providing a peach skin feel and leaves the skin texture even and homogeneous; 92.5% of the survey participants perceived that the composition provides natural radiance to the skin and gives it a healthy appearance; 90.0% of the survey participants perceived that the composition recovers the natural radiance of the skin; 82.5% of the survey participants perceived that the composition revitalizes the skin (reduces the tired skin aspect); 80.0% of the survey participants perceived that the composition does not leave the skin oily; 70.0% of the survey participants perceived that the composition provides an immediate firmness sensation to the skin (immediate tensor effect); 62.5% of the survey participants perceived that the composition immediately disguises fine expression lines and wrinkles.

Example 17. Evaluation of the Anti-Aging Efficacy Through Instrumental Measurements Under Normal Use Conditions—(60+) Day Care Compositions The aim of the study was to assess the efficacy of the compositions according to the present invention in reducing wrinkles and improving skin texture when applied as recommended by means of instrumental evaluations after 14±2 days, 28±2 days and 56±2 days of use.

The survey participants rested in a temperature- and moisture-controlled room for 30 minutes before the baseline measurements and during the interval between measurements. On D0, D14, D28 and D56, 7 consecutive images of the periorbital region were obtained using Optical 3D Skin Measuring Device PRI MOS Compact 5.075 for evaluating wrinkles/texture on one side of the face and 3 (front and side) images using Visia CR (Canfield Scientific, Inc.) that were used for registration purposes.

Figure 12:
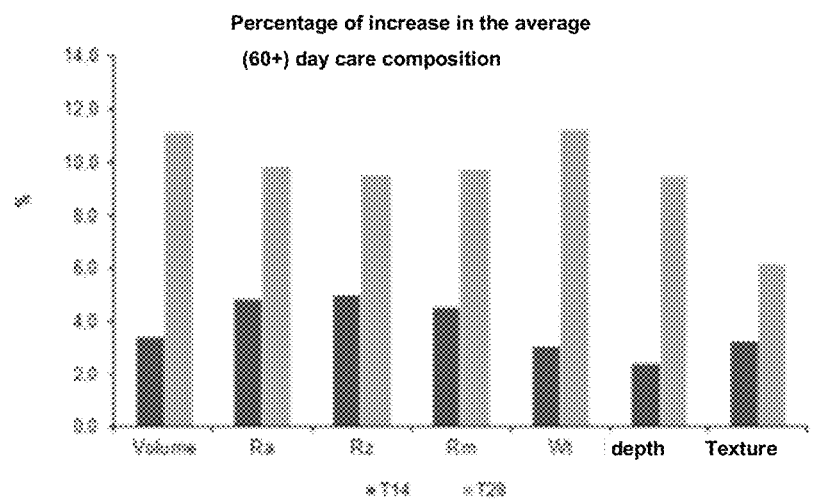
FIGS. 12 and 13 show the percentage of improvement in the anti-aging efficacy of anti-aging (60+) cosmetic day care compositions according to the present invention by means of instrumental measurements under normal use conditions.
Figure 13:
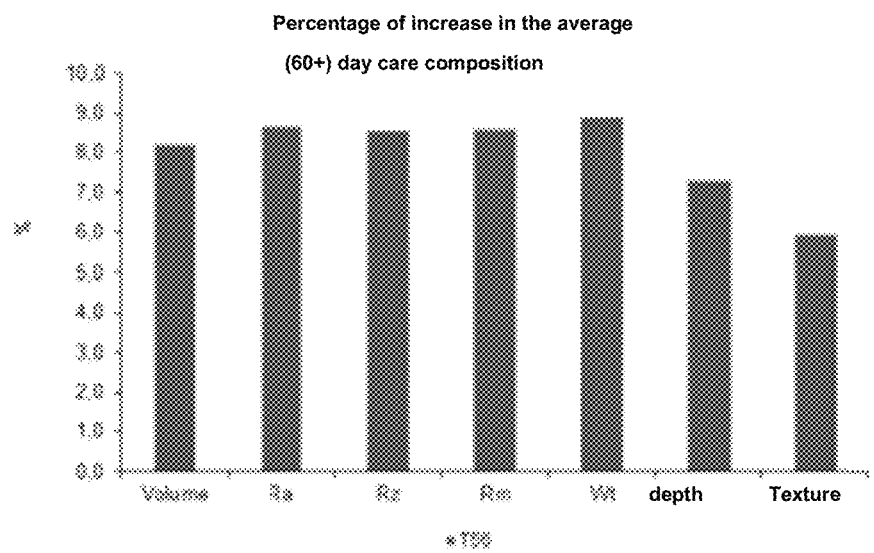
Figure 14:
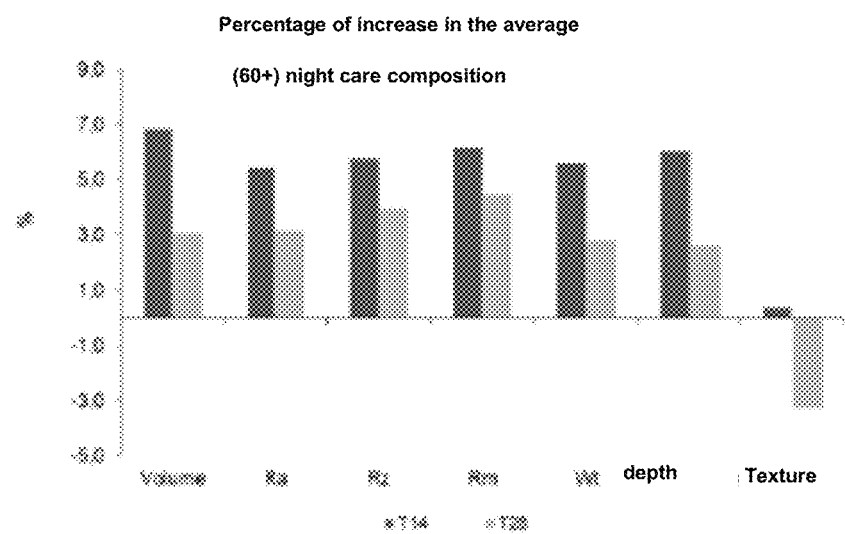
FIGS. 14 and 15 show the percentage of improvement in the anti-aging efficacy of anti-aging (60+) cosmetic night care compositions according to the present invention by means of instrumental measurements under normal use conditions.
Figure 15:
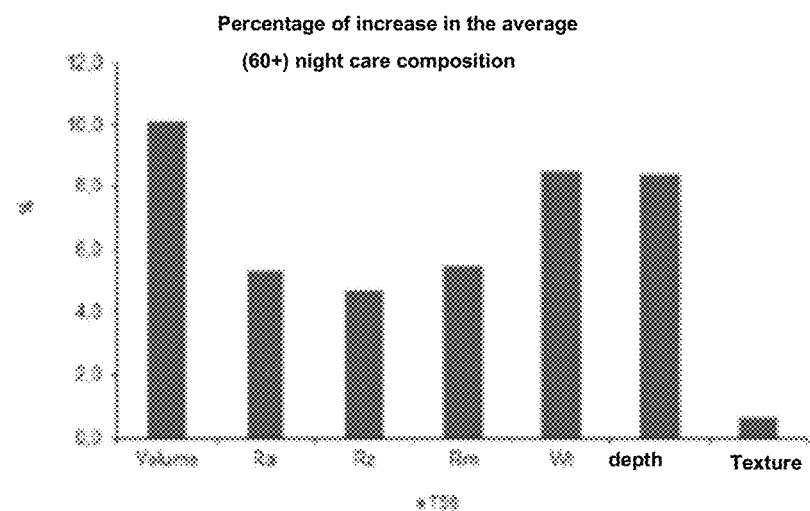

According to the methodology used to assess efficacy, it was concluded that relatively to the baseline (D0):
  The tested composition caused a reduction in the wrinkle volume after twenty-eight and fifty-six days of use;
  The tested composition caused a reduction in the average roughness of the wrinkles after fourteen, twenty-eight and fifty-six days of use;
  The tested composition caused a reduction in the average depth of the wrinkles after fourteen, twenty-eight and fifty-six days of use;
  The tested composition caused a reduction in the maximum roughness of the wrinkles after fourteen, twenty-eight and fifty-six days of use;
  The tested composition caused a reduction in skin undulation after twenty-eight and fifty-six days of use;
  The tested composition caused a reduction in wrinkle depth after twenty-eight and fifty-six days of use;
  The tested composition caused an improvement in skin texture after twenty-eight and fifty-six days of use.
The results are shown in FIGS. 12 and 13.

Example 18. Evaluation of the Anti-Aging Efficacy Through Instrumental Measurements Under Normal Use Conditions—(60+) Night Care Compositions The aim of the study was to assess the efficacy in reducing wrinkles and improving skin texture when applied as recommended, by means of instrumental evaluations after 14±2 days, 28±2 days and 56±2 days of use.

35 participants (female, aged 60 to 69 years, (average age: 64 years), phototypes I to IV, showing wrinkles or expression lines on the periorbital region and all skin types) were left to rest in a temperature- and moisture-controlled room for 30 minutes before taking the baseline measurements and in the interval between measurements. On D0, D14, D28 and D56, 7 consecutive images of the periorbital region were obtained using Optical 3D Skin Measuring Device PRI MOS Compact 5.075 for evaluating wrinkles/texture on one side of the face and 3 (front and side) images using Visia CR (Canfield Scientific, Inc.) that were used for registration purposes.

According to the methodology used to assess efficacy, it was concluded that relatively to the baseline (D0):
  The tested composition caused a reduction in the wrinkle volume after fourteen and fifty-six days of use;
  The tested composition caused a reduction in the average roughness of the wrinkles after fourteen, twenty-eight and fifty-six days of use;
  The tested composition caused a reduction in the average depth of the wrinkles after fourteen, twenty-eight and fifty-six days of use;
  The tested composition caused a reduction in the maximum roughness of the wrinkles after fourteen, twenty-eight and fifty-six days of use;
  The tested composition caused a reduction in skin undulation after fourteen and fifty-six days of use;

The tested composition caused a reduction in wrinkle depth after fourteen and fifty-six days of use;
The tested composition caused an improvement in skin texture after twenty-eight days of use.

Example 19. Evaluation of the Skin Barrier Fortifying Effect Provided by the Use of a Cosmetic Product—(60+) Composition Skin barrier fortification after 7, 14 and 28 days of home use of the compositions according to the present invention was assessed.

26 survey participants (woman who have completed the study; average age: 46±10 years) were assessed as to the transepidermal water loss from the skin after a process of partial removal of the corneous extract in the beginning of the study and after 7, 14 and 28 days of use of the composition.

A tape-stripping process was used to assess the skin barrier fortifying effect, where a transparent medical adhesive tape (Transore 3M, 3M, Brazil) was applied and removed 30 times repeatedly on sites marked on the volar forearm, followed by measuring the transepidermal water loss (Tewameter® 300 and Multiprobe Adapter MPA-5, CKeletronics, Germany). The forearm on which the composition was applied and the control one were randomly selected. One forearm, which was identified with a satin ribbon bracelet, was used for application of the composition, while the other forearm remained as control (without the application of any products).

To do so, application of a sufficient amount of the product on the forearm marked with a satin ribbon bracelet wrapped around the wrist was recommended.

According to the achieved results, the composition applied to the volar forearm skin provided a significant effect of skin barrier fortification as compared to the control after 14 and 28 days of home use. The percent value of skin barrier fortification over the baseline skin condition and the control was 16.0% and 19.3% after 14 and 28 days of home use, respectively. 81% of the survey participants exhibited fortification of the skin barrier after home use of the investigated composition.

Figure 16:
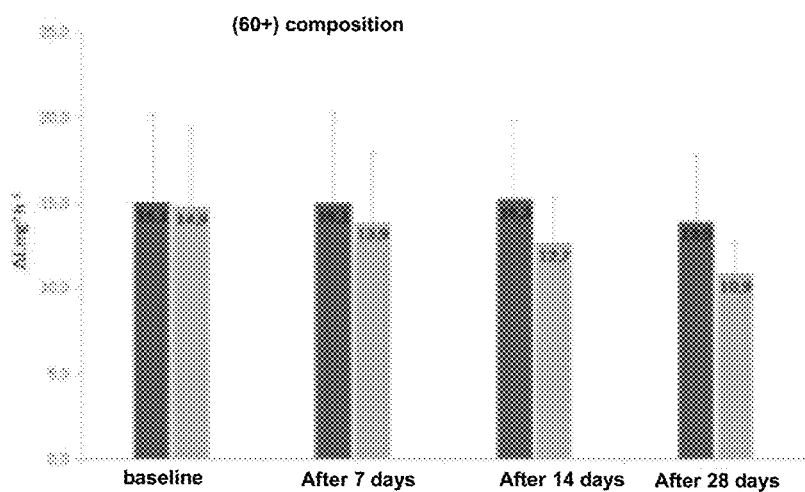
FIG. 16 shows the average variation in transepidermal water loss from skin obtained in the beginning of the study and after 7, 14 and 28 days of use of the (60+) compositions according to the present invention (lighter bars) over the control (darker bars), mean±SD, n=26.
Figure 17:
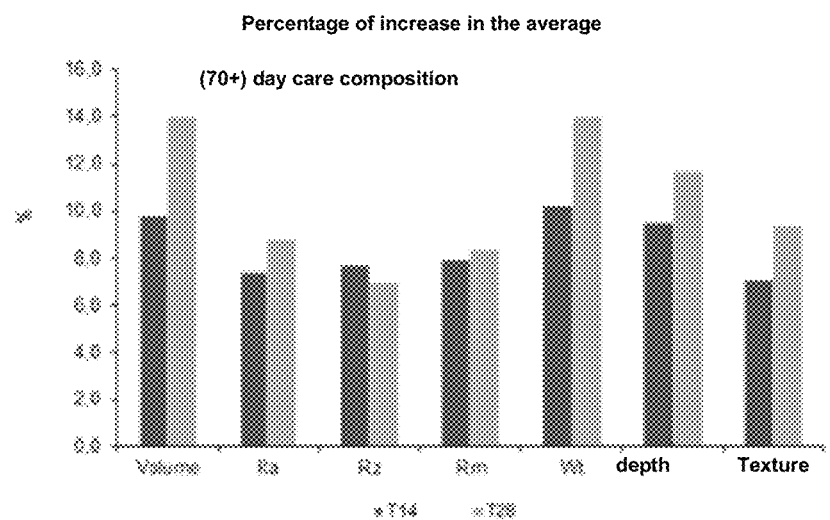
FIGS. 17 and 18 show the percentage of improvement in the anti-aging efficacy of anti-aging (70+) cosmetic day care compositions according to the present invention by means of instrumental measurements under normal use conditions.
Figure 18:
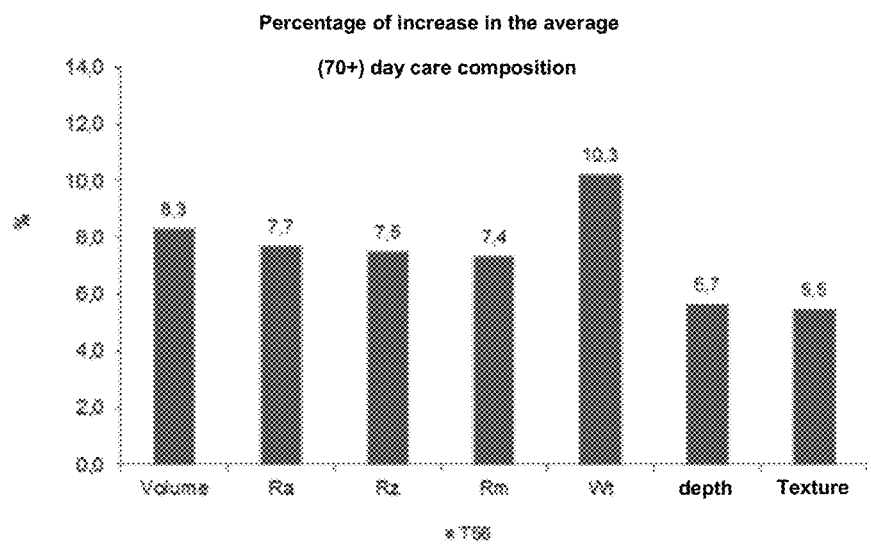
Figure 19:
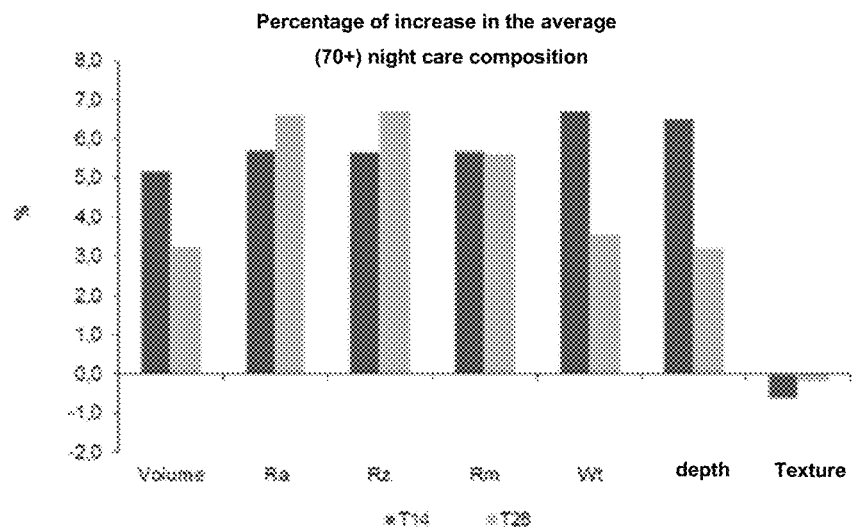
FIGS. 19 and 20 show the percentage of improvement in the anti-aging efficacy of anti-aging (70+) cosmetic night care compositions according to the present invention by means of instrumental measurements under normal use conditions.
Figure 20:
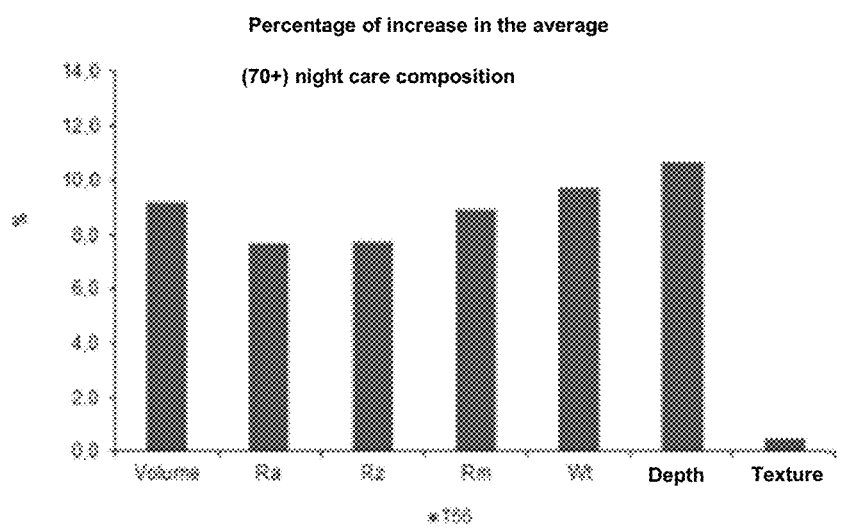

FIG. 16 illustrates the average variation in transepidermal water loss from the skin ($\Delta EDi$) versus time (i=0, 7, 14 or 28 days), obtained for the investigated composition and the control.

According to the study protocol and procedures used to assess the skin barrier fortifying effect provided by applying the composition under investigation on the forearm skin, it has been found that:
it has provided a significant skin barrier fortification effect as compared to the control (skin with no products applied) after 14 and 28 days of home use.
the percent values of skin barrier fortification achieved over the baseline skin condition and control were: 16.0% after 14 days and 19.3% after 28 days of home use.
81% of the survey participants exhibited fortification of the skin barrier after home use of the investigated composition.

Example 20. Evaluation of the Anti-Aging Efficacy of a Cosmetic Product Through Instrumental Measurements Under Normal Use Conditions—(70+) Day Care Compositions The aim of the study was to assess the efficacy of the compositions according to the present invention in reducing wrinkles and improving skin texture when applied as recommended by means of instrumental evaluations after 14±2 days, 28±2 days and 56±2 days of use.

34 participants (female, aged 70 to 79 years, (average age: 73 years), phototypes I to IV, showing wrinkles or expression lines on the periorbital region and all skin types) were left to rest in a temperature- and moisture-controlled room for 30 minutes before taking the baseline measurements and in the interval between measurements. On D0, D14, D28 and D56, 7 consecutive images of the periorbital region were obtained using Optical 3D Skin Measuring Device PRIMOS Compact 5.075 for evaluating wrinkles/texture on one side of the face and 3 (front and side) images using Visia CR (Canfield Scientific, Inc.) that were used for registration purposes.

According to the methodology used to assess efficacy, it was concluded that relatively to the baseline (D0):
The compositions according to the present invention caused a reduction in the wrinkle volume after fourteen, twenty-eight and fifty-six days of use;
The compositions according to the present invention caused a reduction in the average roughness of the wrinkles after fourteen, twenty-eight and fifty-six days of use;
The compositions according to the present invention caused a reduction in the average depth of the wrinkles after fourteen, twenty-eight and fifty-six days of use;
The compositions according to the present invention caused a reduction in the maximum wrinkle roughness after fourteen, twenty-eight and fifty-six days of use;
The compositions according to the present invention caused a reduction in the skin undulation after fourteen, twenty-eight and fifty-six days of use;
The compositions according to the present invention caused a reduction in wrinkle depth after fourteen, twenty-eight and fifty-six days of use; and
The compositions according to the present invention caused an improvement in skin texture after fourteen, twenty-eight and fifty-six days of use.

Example 21. Evaluation of the Anti-Aging Efficacy of a Cosmetic Product Through Instrumental Measurements Under Normal Use Conditions—(70+) Night Care Compositions The aim of the study was to assess the efficacy in reducing wrinkles and improving skin texture when applied as recommended, by means of instrumental evaluations after 14±2 days, 28±2 days and 56±2 days of use.

35 participants (female, aged 70 to 79 years, average age: 73 years), phototypes I to IV, showing wrinkles or expression lines on the periorbital region and all skin types) were left to rest in a temperature- and moisture-controlled room for 30 minutes before taking the baseline measurements and in the interval between measurements.

On D0, D14, D28 and D56, 7 consecutive images of the periorbital region were obtained using Optical 3D Skin Measuring Device PRIMOS Compact 5.075 for evaluating wrinkles/texture on one side of the face and 3 (front and side) images using Visia CR (Canfield Scientific, Inc.) that were used for registration purposes.

According to the methodology used to assess efficacy, it was concluded that relatively to the baseline (D0):
The composition according to the present invention caused a reduction in the wrinkle volume after fourteen, twenty-eight and fifty-six days of use;

The composition according to the present invention caused a reduction in the average roughness of the wrinkles after fourteen, twenty-eight and fifty-six days of use;

The composition according to the present invention caused a reduction in the average depth of the wrinkles after fourteen, twenty-eight and fifty-six days of use;

The composition according to the present invention caused a reduction in the maximum wrinkle roughness after fourteen, twenty-eight and fifty-six days of use;

The composition according to the present invention caused a reduction in wrinkle undulation after fourteen, twenty-eight and fifty-six days of use; and The composition according to the present invention caused a reduction in the wrinkle depth after fourteen and fifty-six days of use.

Example 22. Evaluation of the Skin Barrier Fortifying Effect Provided by the (70+) Compositions According to the Present Invention—Day Care Compositions 25 survey participants (woman who have completed the study; average age: 42±11 years.) There were no reports or evidence of adverse reaction during the study.

The methodology consisted of assessing the transepidermal water loss from the skin after a process of partial removal of the corneous extract in the beginning of the study and after 7, 14 and 28 days of use of the composition. A tape-stripping process was used to assess the skin barrier fortifying effect, where a transparent medical adhesive tape (Transore 3M, 3M, Brazil) was applied and removed 30 times repeatedly on sites marked on the volar forearm, followed by measuring the transepidermal water loss (Tewameter® 300 and Multiprobe Adapter MPA-5, CKeletronics, Germany). The forearm on which the composition was applied and the control one were randomly selected. One forearm, which was identified with a satin ribbon bracelet, was used for application of the composition, while the other forearm remained as control (without the application of any products).

According to the achieved results, the composition applied to the volar forearm skin provided a significant effect of skin barrier fortification as compared to the control after 7, 14 and 28 days of home use. The percent value of skin barrier fortification over the baseline skin condition and the control was 14.5% after 7 days, 21.1% after 14 days and 25.0% after 28 days of home use. 88.0% of the survey participants exhibited fortification of the skin barrier after home use of the investigated composition.

Figure 21:
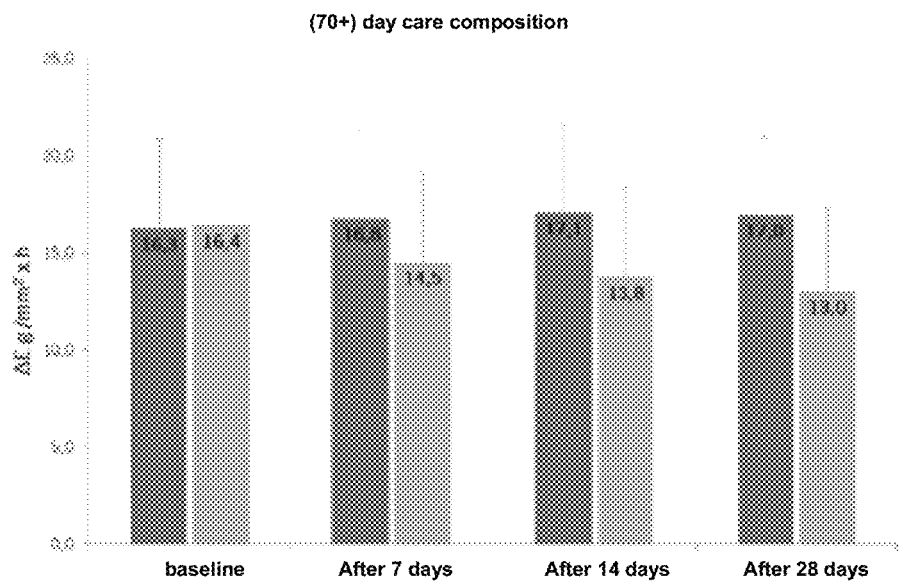
FIGS. 21 and 22 show the average variation in transepidermal water loss from the skin obtained in the beginning of the study and after 7, 14 and 28 days of use of the composition (lighter bars) relative to the control (darker bars), Mean±SD, n=25, for day and night care (70+) compositions, respectively.

FIG. 21 shows the average variation in transepidermal water loss from the skin obtained in the beginning of the study and after 7, 14 and 28 days of use of the (45+) composition over control (Mean±SD, n=25).

Example 23. Evaluation of the Skin Barrier Fortifying Effect Provided by the Use of a Cosmetic Product—(70+) Night Care Compositions 26 survey participants (woman who have completed the study; average age: 44±11 years.)

The methodology consisted of assessing the transepidermal water loss from the skin after a process of partial removal of the corneous extract in the beginning of the study and after 7, 14 and 28 days of use of the composition. A tape-stripping process was used to assess the skin barrier fortifying effect, where a transparent medical adhesive tape (Transore 3M, 3M, Brazil) was applied and removed 30 times repeatedly on sites marked on the volar forearm, followed by measuring the transepidermal water loss (Tewameter® 300 and Multiprobe Adapter MPA-5, CKeletronics, Germany). The forearm on which the composition was applied and the control one were randomly selected. One forearm, which was identified with a satin ribbon bracelet, was used for application of the composition, while the other forearm remained as control (without the application of any products).

According to the achieved results, the composition applied to the volar forearm skin provided a significant effect of skin barrier fortification as compared to the control after 7, 14 and 28 days of home use. The percent value of skin barrier fortification over the baseline skin condition and the control was 13.0% after 7 days, 18.6% after 14 days and 27.9% after 28 days of home use. 84.6% of the survey participants exhibited skin barrier fortification after home use of the composition.

Figure 22:
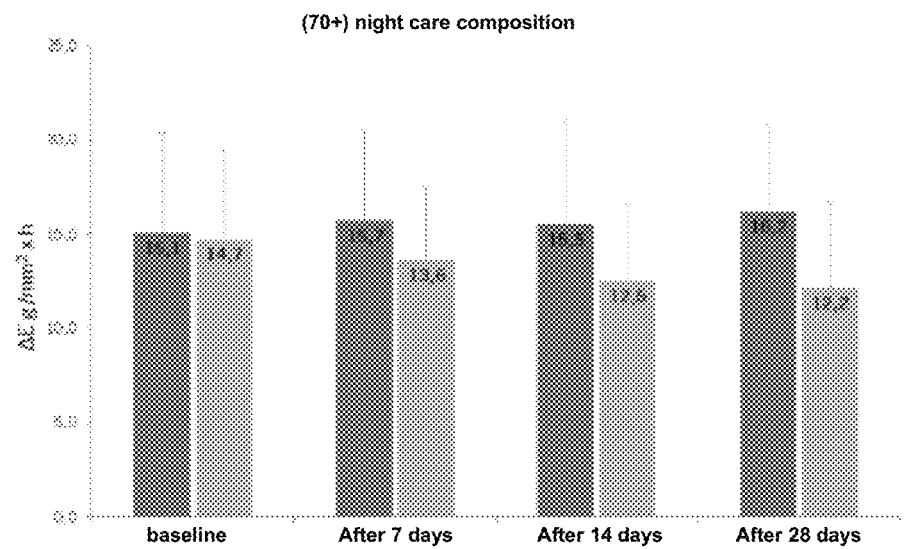

FIG. 22 shows the average variation in transepidermal water loss from the skin obtained in the beginning of the study and after 7, 14 and 28 days of use of the composition over control (Mean±SD, n=26).

The person skilled in the art, by means of the teachings of the text and examples disclosed herein, will readily appreciate the advantages of the invention and will propose equivalent embodiment variations and alternatives without departing from the scope of the invention as defined in the appended claims.

The invention claimed is:

1. An anti-aging cosmetic composition comprising an oil-in-water emulsion, the oil-in-water emulsion comprising:

a) at least one emollient selected from the group consisting of caprylyl methicone, $C_{12-15}$ alkyl benzoate, dibutyl adipate, dicaprylyl carbonate, isononyl isononanoate, dicapryl ether, dodecane, ethylhexyl palmitate, ethyl macadamate, isohexadecane, capric/caprylic triglyceride, butters from the Brazilian biodiversity, isoamyl cocoate, and mixtures thereof, wherein the butters from the Brazilian biodiversity are selected from the group consisting of murumuru butter, cocoa butter, cupuacu butter, ucuitba butter, sapucainha butter, and mixtures thereof;

b) at least one antioxidant selected from the group consisting of butylated hydroxytoluene (BHT), tocopherol acetate, natural plant extracts, and mixtures thereof, wherein the natural plant extract comprises *Theobroma cacao* (cocoa);

c) at least one humectant comprising one or more sugar alcohols, wherein the one or more sugar alcohols are selected from the group consisting of sorbitol, mannitol, vegetable glycerin, and mixtures thereof;

d) *Camellia sinensis* (green tea) and *Spilanthes acmella* and optionally a complex of acetyl tetrapeptide-2/caprylyl glycol/water;

e) at least one emulsifier selected from the group consisting of glyceryl stearate citrate, potassium cetylphosphate, PEG-100, acrylates, xanthan gum, cetearyl alcohol, a mixture of glyceryl stearate/PEG-100, and mixtures thereof;

f) at least one sensory modifier selected from the group consisting of cyclopentasiloxane, cyclopentasiloxane/dimethicone crosspolymers, titanium isopropyl tri-isostearate, nylon-12, polymethylsilsesquioxane, aluminum starch octenylsuccinate, and mixtures thereof; and g) one or more cosmetically acceptable carriers.

2. The composition of claim 1, further comprising a viscosity donor selected from a group consisting of a crosspolymer of acrylate/$C_{10-30}$ alkyl acrylate, carbopol, a mixture of hydroxyethyl acrylate/copolymer of sodium acryloyldimethyltaurate, squalene, polysorbate 60, and mixtures thereof.

3. The composition of claim 1, further comprising at least one sunscreen.

4. The composition of claim 3, wherein the sunscreen is selected from the group consisting of diethylaminohydroxybenzoylhexyl benzoate, ethylhexylmethoxy cinnamate, homosalate, bisoctrizole, ethylhexyl triazone, and mixtures thereof.

5. A system of compositions comprising the anti-aging cosmetic composition of claim 1 and an active ingredient for stimulating skin regeneration.

6. A method for cosmetic treatment of the skin, the method comprising applying the composition of claim 1 on the skin to be treated, wherein the applying step occurs during the day and/or at night.

* * * * *

UNITED STATES PATENT AND TRADEMARK OFFICE
CERTIFICATE OF CORRECTION

PATENT NO. : 11,478,409 B2
APPLICATION NO. : 16/304530
DATED : October 25, 2022
INVENTOR(S) : Fabiana Paes et al.

It is certified that error appears in the above-identified patent and that said Letters Patent is hereby corrected as shown below:

On the Title Page

Item (73), Assignee, delete "Natura Cosmeticos S.A., Sao Paula (BR)" and insert -- Natura Cosméticos S.A., São Paulo (BR) --, therefor.

Signed and Sealed this
Eleventh Day of July, 2023

Katherine Kelly Vidal
*Director of the United States Patent and Trademark Office*